(12) United States Patent
Furuya et al.

(10) Patent No.: US 12,142,249 B2
(45) Date of Patent: Nov. 12, 2024

(54) INFORMATION PROCESSING APPARATUS

(71) Applicant: SONY GROUP CORPORATION, Tokyo (JP)

(72) Inventors: Shinichi Furuya, Tokyo (JP); Takanori Oku, Tokyo (JP)

(73) Assignee: SONY GROUP CORPORATION, Tokyo (JP)

( * ) Notice: Subject to any disclaimer, the term of this patent is extended or adjusted under 35 U.S.C. 154(b) by 796 days.

(21) Appl. No.: 17/281,033

(22) PCT Filed: Sep. 20, 2019

(86) PCT No.: PCT/JP2019/036945
§ 371 (c)(1),
(2) Date: Mar. 29, 2021

(87) PCT Pub. No.: WO2020/071149
PCT Pub. Date: Apr. 9, 2020

(65) Prior Publication Data
US 2021/0350773 A1   Nov. 11, 2021

(30) Foreign Application Priority Data
Oct. 5, 2018   (JP) ................. 2018-190061

(51) Int. Cl.
*G10G 1/00*        (2006.01)
*A61B 5/0205*      (2006.01)
(Continued)

(52) U.S. Cl.
CPC ............ *G10G 1/00* (2013.01); *A61B 5/0205* (2013.01); *A61B 5/1118* (2013.01); *G06F 3/015* (2013.01);
(Continued)

(58) Field of Classification Search
CPC .......... G10G 1/00; G10G 3/04; A61B 5/0205; A61B 5/1118; A61B 2562/0219; G06F 3/015
See application file for complete search history.

(56) References Cited

U.S. PATENT DOCUMENTS 6,597,350 B1 *  7/2003  Moriguchi ............... G09G 5/18
                                                       345/204
7,446,694 B1    11/2008  Ahmed et al.
(Continued)

FOREIGN PATENT DOCUMENTS

| CN | 101022007 A | 8/2007 |
| CN | 101198277 A | 6/2008 |

(Continued)

*Primary Examiner* — Jianchun Qin
(74) *Attorney, Agent, or Firm* — Paratus Law Group, PLLC

(57) ABSTRACT

There is provided an information processing apparatus that includes a plurality of pieces of sensing data in different forms obtained from a plurality of sensors each sensing a state related to a performance by a motion of a user, an information processing section that processes the sensing data converted by the conversion section, and an information output section that outputs feedback information to the user on the basis of a processing result of the information processing section. The conversion section converts the sensing data in an analog form from the sensors into sensing data in a digital form and outputs the sensing data in the digital form to the information processing section, and converts the sensing data in the digital form from the sensors into sensing data in the analog form and outputs the sensing data in the analog form to the analog-digital signal conversion section.

20 Claims, 11 Drawing Sheets

(51) Int. Cl.
*A61B 5/11* (2006.01)
*G06F 3/01* (2006.01)
*G10G 3/04* (2006.01)

(52) U.S. Cl.
CPC ........ *G10G 3/04* (2013.01); *A61B 2562/0219* (2013.01)

(56) References Cited

U.S. PATENT DOCUMENTS

| | | |
|---|---|---|
| 2011/0215952 A1 | 9/2011 | Aria et al. |
| 2016/0328642 A1 | 11/2016 | Himebaugh et al. |
| 2019/0113973 A1* | 4/2019 | Coleman .................. G06F 3/011 |

FOREIGN PATENT DOCUMENTS

| | | |
|---|---|---|
| CN | 103076045 A | 5/2013 |
| CN | 103957777 A | 7/2014 |
| CN | 104182607 A | 12/2014 |
| CN | 104658358 A | 5/2015 |
| CN | 105575219 A | 5/2016 |
| CN | 106371611 A | 2/2017 |
| CN | 206194191 U | 5/2017 |
| CN | 107302548 A | 10/2017 |
| CN | 107636752 A | 1/2018 |
| CN | 108320613 A | 7/2018 |
| CN | 207732965 U | 8/2018 |
| JP | H07-129880 A | 5/1995 |
| JP | 2003-217064 A | 7/2003 |
| JP | 2009-047861 A | 3/2009 |
| JP | 2009-528909 A | 8/2009 |
| JP | 2017-173589 A | 9/2017 |
| WO | WO 2019/130755 A1 | 7/2019 |

* cited by examiner

F I G . 1 3
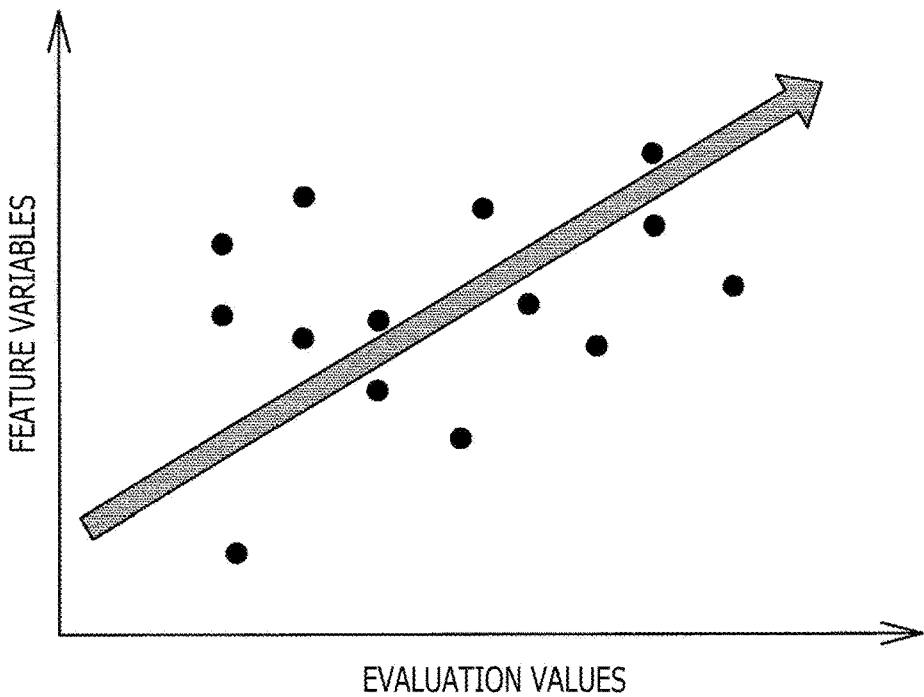
F I G . 1 4
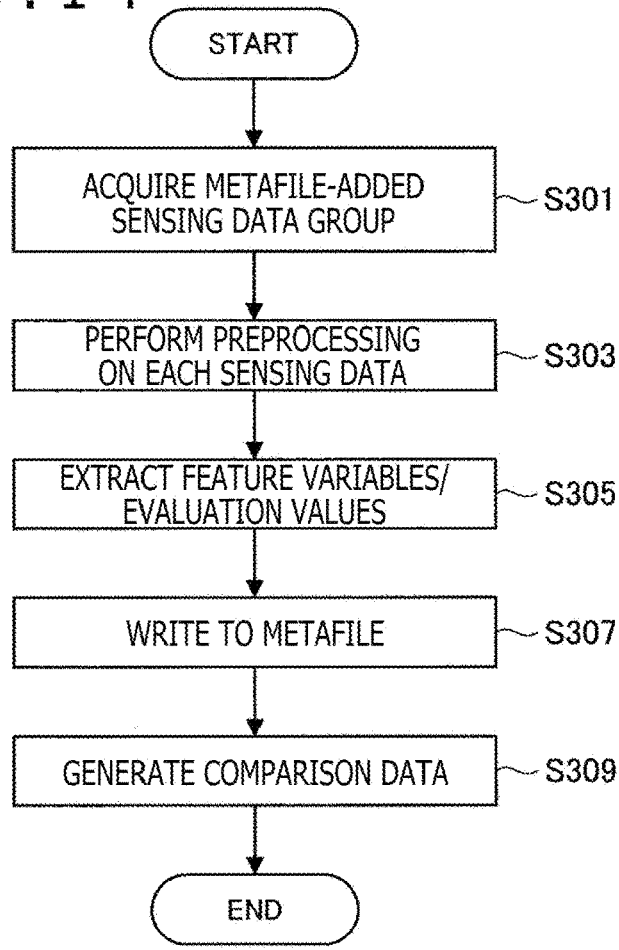

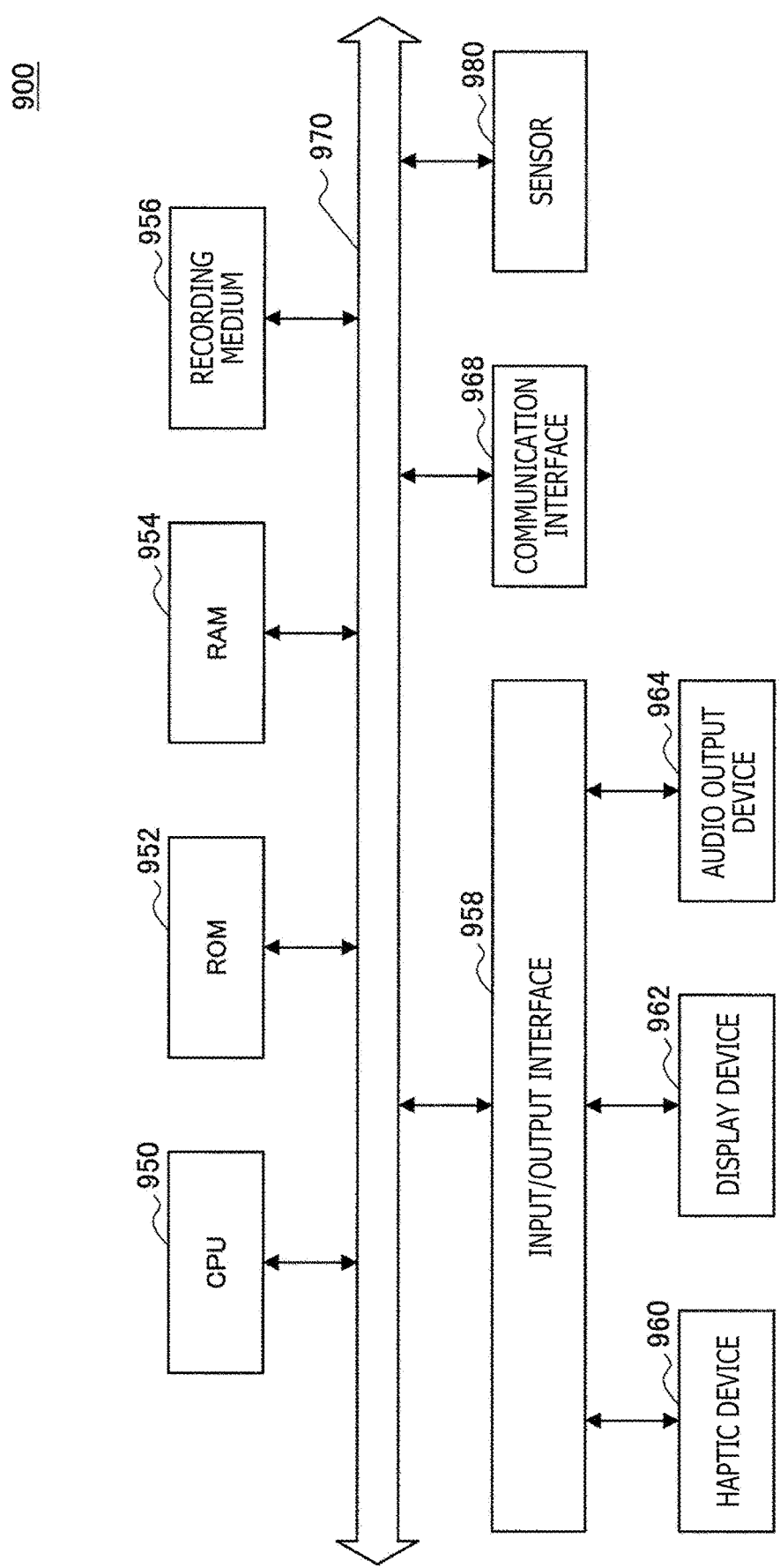

INFORMATION PROCESSING APPARATUS

CROSS REFERENCE TO PRIOR APPLICATION

This application is a National Stage Patent Application of PCT International Patent Application No. PCT/JP2019/036945 (filed on Sep. 20, 2019) under 35 U.S.C. § 371, which claims priority to Japanese Patent Application No. 2018-190061 (filed on Oct. 5, 2018), which are all hereby incorporated by reference in their entirety.

TECHNICAL FIELD

The present disclosure relates to an information processing apparatus.

BACKGROUND ART

In recent years, with the development of miniaturization, simplification, and the like of various types of motion sensors and biological information sensors, it has become easier to acquire various types of sensing data with these sensors, and the sensing data have been used, for example, for assistance of user's learning of a performance (playing of a musical instrument, a sport, and the like). For example, as a technology for evaluating a performance (playing of a musical instrument) and assisting in the performance, a technology disclosed in PTL 1 below can be cited. In such learning assistance, data that can be used in the learning assistance is obtained by acquiring various pieces of sensing data from a plurality of sensors and analyzing the plurality of acquired sensing data.

CITATION LIST

Patent Literature

[PTL 1]
Japanese Patent Laid-open No. 2009-47861

SUMMARY

Technical Problem

Meanwhile, in the case of intending to acquire a plurality of pieces sensing data using a plurality of different types of sensors, the sensing data sometimes differs in form. For example, sensing data from a biological information sensor is normally in an analog form. In such a case, the analog form of the sensing data from the biological information sensor is converted into a digital form to make the sensing data in the form similar to that of sensing data from other sensors, and the sensing data from the biological information sensor in the digital form is then analyzed together with the sensing data from the other sensors. Furthermore, to acquire data useful for the assistance of user's learning of the performance, it is required to accurately synchronize a plurality of pieces of sensing data even in a mixture of forms as described above.

Therefore, the present disclosure proposes a novel and improved information processing apparatus capable of accurately synchronizing and handling sensing data in a mixture of forms and available for assisting in learning of a performance.

Solution to Problem

The present disclosure provides an information processing apparatus including a conversion section that converts a plurality of pieces of sensing data in different forms obtained from a plurality of sensors each sensing a state related to a performance by a motion of a user, an information processing section that processes the sensing data converted by the conversion section, and an information output section that outputs feedback information to the user on the basis of a processing result of the information processing section. The conversion section includes an analog-digital signal conversion section that converts the sensing data in an analog form from the sensors into sensing data in a digital form and outputs the sensing data in the digital form to the information processing section, and a digital-analog signal conversion section that converts the sensing data in the digital form from the sensors into sensing data in the analog form and outputs the sensing data in the analog form to the analog-digital signal conversion section.

Advantageous Effect of the Invention

As described so far, according to the present disclosure, it is possible to provide an information processing apparatus capable of accurately synchronizing and handling sensing data in a mixture of forms and available for assisting in learning of a performance.

It is noted that effects are not always limited to the above effect, the present disclosure may exhibit any of the effects described in the present specification or other effects that can be conceived from the present specification in addition to or as an alternative to the above effect.

BRIEF DESCRIPTION OF DRAWINGS

FIG. 13 is an explanatory diagram (2) of the example of creating training data.

FIG. 14 is a flowchart of creating comparison data according to the embodiment of the present disclosure.

FIG. 19 is an explanatory diagram of an example of a hardware configuration of an information processing apparatus 900 according to the embodiment of the present disclosure.

DESCRIPTION OF EMBODIMENTS

Figure 1:
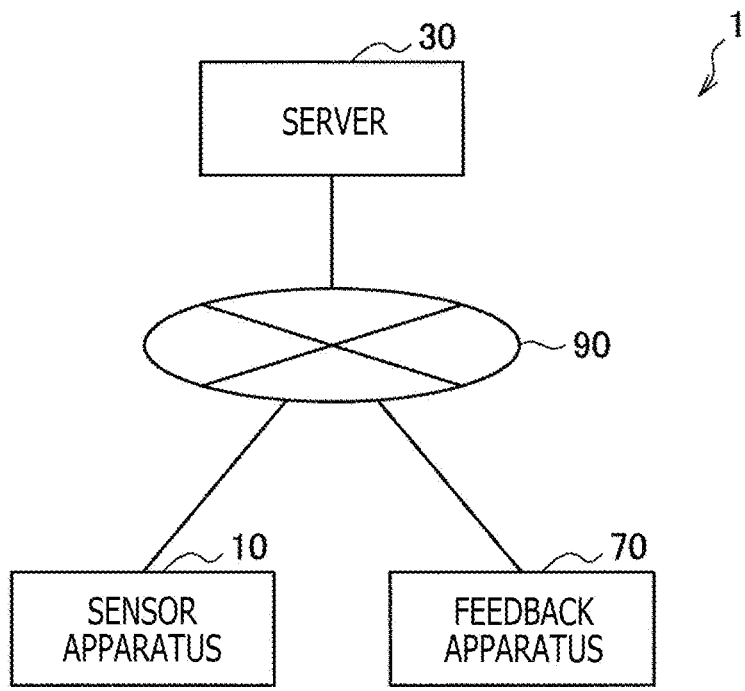
FIG. 1 is an explanatory diagram of an example of a configuration of an information processing system 1 according to an embodiment of the present disclosure.

A preferable embodiment of the present disclosure will be described hereinafter in detail with reference to the accompanying drawings. It is noted that, in the present specification and drawings, repetitive description will be omitted by denoting constituent elements having substantially identical functional configurations by the same reference sign.

Furthermore, in the present specification and drawings, a plurality of constituent elements having substantially the same or similar functional configurations is sometimes distinguished from one another by putting different numbers after the same reference sign. However, in the case of no need to particularly distinguish the plurality of constituent elements having substantially the same or similar functional configurations, the constituent elements are denoted only by the same reference sign. Moreover, similar constituent elements in different embodiments are sometimes distinguished from one another by putting different alphabets after the same reference sign. However, in the case of no need to particularly distinguish the similar constituent elements, the constituent elements are denoted only by the same reference sign.

It is noted that the description is given in the following order.

1. Circumstances until inventors of present disclosure reached to creation of embodiment according to present disclosure
2. Embodiment of present disclosure
   2.1. Outline of information processing system 1 according to embodiment of present disclosure
   2.2. Configuration of sensor apparatus 10 according to embodiment of present disclosure
   2.3. Configuration of server 30 according to embodiment of present disclosure
   2.4. Configurations of conversion apparatus 20 and computing apparatus 26 according to embodiment of present disclosure
   2.5. Configuration of feedback apparatus 70 according to embodiment of present disclosure
   2.6. Information processing method according to embodiment of present disclosure
   2.6.1 Details of creation of training data
   2.6.2 Details of creation of comparison data
   2.6.3 Details of comparison
   2.7. Summary
3. Learning assistance mode
4. Examples of application of embodiment of present disclosure
5. Hardware configuration
6. Supplemental remarks

1. Circumstances Until Inventors of Present Disclosure Reached to Creation of Embodiment According to Present Disclosure Before starting description of an embodiment according to the present disclosure, circumstances until the inventors of the present disclosure reached to creation of the embodiment according to the present disclosure will first be described.

As previously described, in recent years, with the development of miniaturization, simplification, and the like of various types of motion sensors and biological information sensors, it has become easier to acquire various types of sensing data with these sensors, and the sensing data have been used, for example, for assistance of user's learning of a performance (playing of a musical instrument, a sport, and the like). In such learning assistance, data that can be used in the learning assistance is obtained by acquiring various pieces of sensing data from a plurality of sensors simultaneously in real time and analyzing the plurality of acquired sensing data.

Furthermore, in the case of performing such analysis, it is required to match timings of acquiring the sensing data and sensing time widths of the plurality of sensors with one another, that is, to synchronize the plurality of pieces of sensing data with one another. It is assumed that "synchronize/synchronization" means to match the timings of acquiring sensing data and the sensing time widths of the plurality of sensing data with one another in the following description.

Meanwhile, the sensing data from the biological information sensors are normally in an analog form such as waveform data varying with the passage of time. On the other hand, many sensors or electronic musical instruments and the like used by a user normally output sensing data or data in a digital form. To cope with the difference, in the learning assistance as described above, for purposes of simultaneously analyzing these plurality of pieces of sensing data, the sensing data in the analog form is converted into sensing data in the digital form by an analog-digital signal converter or the like before analysis. It is, therefore, required to accurately synchronize even the plurality of pieces of sensing data in a mixture of forms as described above so as to acquire data useful for the assistance of user's learning of the performance.

However, the plurality of pieces of sensing data is subjected to conversion as described above due to the difference in form; thus, it is difficult to accurately synchronize these plurality of pieces of sensing data.

In light of such circumstances, therefore, the inventors of the present disclosure have reached to creation of the embodiment of the present disclosure capable of accurately synchronizing and handling sensing data in a mixture of forms and available for the assistance of learning of a performance. An information processing system and an information processing method according to the embodiment of the present disclosure described above will be described hereinafter in sequence and in detail.

It is noted that the embodiment of the present disclosure will be described hereinafter regarding the case of applying the embodiment to guidance (learning of a skill) of a piano playing technique. However, application of the embodiment of the present disclosure is not limited to the guidance of the piano playing technique, and the embodiment of the present disclosure is applicable to playing techniques of other musical instruments, learning of skills of sports and traditional arts and crafts, rehabilitation of an impaired motility function, and the like. Furthermore, in the embodiment of the present disclosure, the musical instrument is not limited to the piano but may be every type of electronic musical instrument or every type of acoustic musical instrument.

Furthermore, in the following description, examples of a user include a learner receiving guidance of the piano playing technique and a performer who gives or is to give a performance such as a performer (for example, professional pianist) regarding whom various types of sensing data are collected in constructing a database according to the present embodiment, and also include an instructor or the like using the information processing system according to the present embodiment.

Moreover, in the following description, it is assumed that evaluation values (evaluation information) for a piano performance (performance) mean a performance speed (a pace, a rhythm) of the performer in the performance, accuracy of the performance (accuracy of the rhythm or of a volume of each tone), a volume of a sound generated by the performance (a peak of a sound waveform), a sound vibration (an integral value of the sound waveform), a timbre (a spectrum), a volume difference and a temporal difference (so-called "balance" in a chord (a group of musical notes)) among musical tones in the chord, a difference (range) between a maximum value and a minimum value of each sound parameter, a granularity (a resolution) of each sound parameter, energy efficiency in the performance, and the like. Furthermore, in the following description, parameters in a trade-off relation (for example, the performance speed and the accuracy) are present among the plurality of parameters described above; thus, in consideration of such a case, the evaluation values of the piano performance may be proportions of the parameters (numerical values). In general, an instructor gives guidance while placing greater importance on preferentially learning the performance accuracy than on the performance speed for the following reasons. In a case in which the learner repeats performances with many false motions and low accuracy while keeping a high performance speed, the body, cranial nerves, and the like of the learner are caused to learn the false motions. On the other hand, in the case of guidance with excessive importance placed on learning the accuracy, the learner strains himself/herself and falls into a habit of hardening the muscles, causing a reduction in energy efficiency in the performance. In the present embodiment, therefore, the proportions of the parameters may be used as the evaluation values in consideration of the balance of the parameters in the trade-off relation as described above. Moreover, in the case of applying the embodiment of the present disclosure not only to the piano performance but also to other user motions, the evaluation values of the performance may be a motion pattern of a motion element made by the user, a motion velocity, motion accuracy, a quantity of motion (motion power, an impulse, an amount of work, and the like), energy efficiency in the performance, a state of a result generated by the performance, and the like.

Furthermore, in the following description, synchronizing a plurality of pieces of sensing data means to match timings of acquisition and processing of the plurality of pieces of sensing data with one another and to match time widths of the plurality of pieces of sensing data with one another.

Additionally, in the following description, performing one test piece (for example, a music, a phrase, a scale, an arpeggio, a chord, or the like) by one performer or one learner is referred to as "one trial." It is noted that, in the embodiment of the present disclosure, it is possible to acquire a plurality of pieces of sensing data in one trial.

2. Embodiment of Present Disclosure 2.1. Outline of Information Processing System 1 According to Embodiment of Present Disclosure A schematic configuration of an information processing system (information processing apparatus) 1 according to the embodiment of the present disclosure will first be described with reference to FIG. 1. FIG. 1 is an explanatory diagram of an example of a configuration of the information processing system 1 according to the present embodiment. In the information processing system 1 according to the present embodiment, a server (information processing section) 30 analyzes a plurality of pieces of sensing data obtained from a plurality of sensor apparatuses (sensors) 10 that senses a state related to a performance given by moving of a user (learner or performer). Furthermore, the information processing system 1 feeds back information in various forms to the user via a feedback apparatus (information output section) 70 on the basis of a result of the analysis described above.

As depicted in FIG. 1, the information processing system 1 according to the present embodiment includes the sensor apparatus 10, the server 30, and the feedback apparatus 70, and these apparatuses are communicably connected to one another via a network 90. For example, the sensor apparatus 10, the server 30, and the feedback apparatus 70 may be connected to the network 90 via base stations or the like not depicted (for example, base stations of cellular telephones or access points of a wireless LAN (Local Area Network)). In other words, any scheme, regardless of wired or wireless, can be applied to a communication scheme used in the network 90. An outline of each apparatus included in the information processing system 1 according to the present embodiment will be described hereinafter.

(Sensor Apparatus 10)

The sensor apparatus 10 can sense a state related to a performance according to a motion of the performer or the learner. More specifically, the sensor apparatus 10 can be every type of biological information sensor that can be attached to a part of a body of the learner or the performer, an imaging apparatus that images the learner or the performer, a pressure sensor or a photoreflector sensor provided in the piano played by the learner or the performer, a sound pick-up apparatus (for example, a microphone) that collects the sound of the piano, or the like. Furthermore, the sensor apparatus 10 may be an electronic musical instrument such as an electronic piano per se capable of outputting signals. Moreover, the number of the sensor apparatuses 10 and a type thereof included in the information processing system 1 according to the present embodiment are not limited to a specific number and a specific type. It is noted that details of the sensor apparatus 10 will be described later.

(Server 30)

The server 30 is configured with, for example, a computer. More specifically, the server 30 collects the sensing data related to the performance of the performer or the learner from the sensor apparatus 10, analyzes and processes the collected sensing data, and outputs information for feedback (feedback information) to the learner or the like on the basis of results of analysis and processing. Furthermore, the server 30 may be, for example, a computer owned by the user, or a computer owned by a service provider that provides services by the present embodiment and that is present in a location different from a location of the user. It is noted that details of the server 30 will be described later.

(Feedback Apparatus 70)

The feedback apparatus 70 is an apparatus for presenting (outputting) the feedback information from the server 30 to the learner or the like, and notifies the learner of the feedback information (outputs the feedback information to the learner) as visible, haptic, auditory, or audible data during or after the performance of the learner. For example, the feedback apparatus 70 can be a device including a display device (display) and an audio output device (speaker) such as a tablet, a smart phone, a laptop PC (Personal Computer), or a notebook PC. Furthermore, the feedback apparatus 70 may be a wearable device that can be attached to a part of the body of the learner. More specifically, as the wearable device, every type of wearable device such as an HMD (Head Mounted Display) type, an ear device (headphone) type, an anklet type, a wristband type, a choker ring type, an eyewear type, a glove type, a pad type, a badge type, and a garment type. It is noted that details of the feedback apparatus 70 will be described later.

While FIG. 1 depicts that the information processing system 1 according to the present embodiment includes one sensor apparatus 10 and one feedback apparatus 70, the configuration of the information processing system 1 according to the present embodiment is not limited to that depicted in FIG. 1. In the present embodiment, the information processing system 1 can include, for example, a plurality of sensor apparatuses 10 and a plurality of feedback apparatuses 70. Furthermore, the information processing system 1 according to the embodiment may include, for example, another communication apparatus such as a relay apparatus used at the time of transmitting the sensing data from the sensor apparatus 10 to the server 30.

Figure 2:
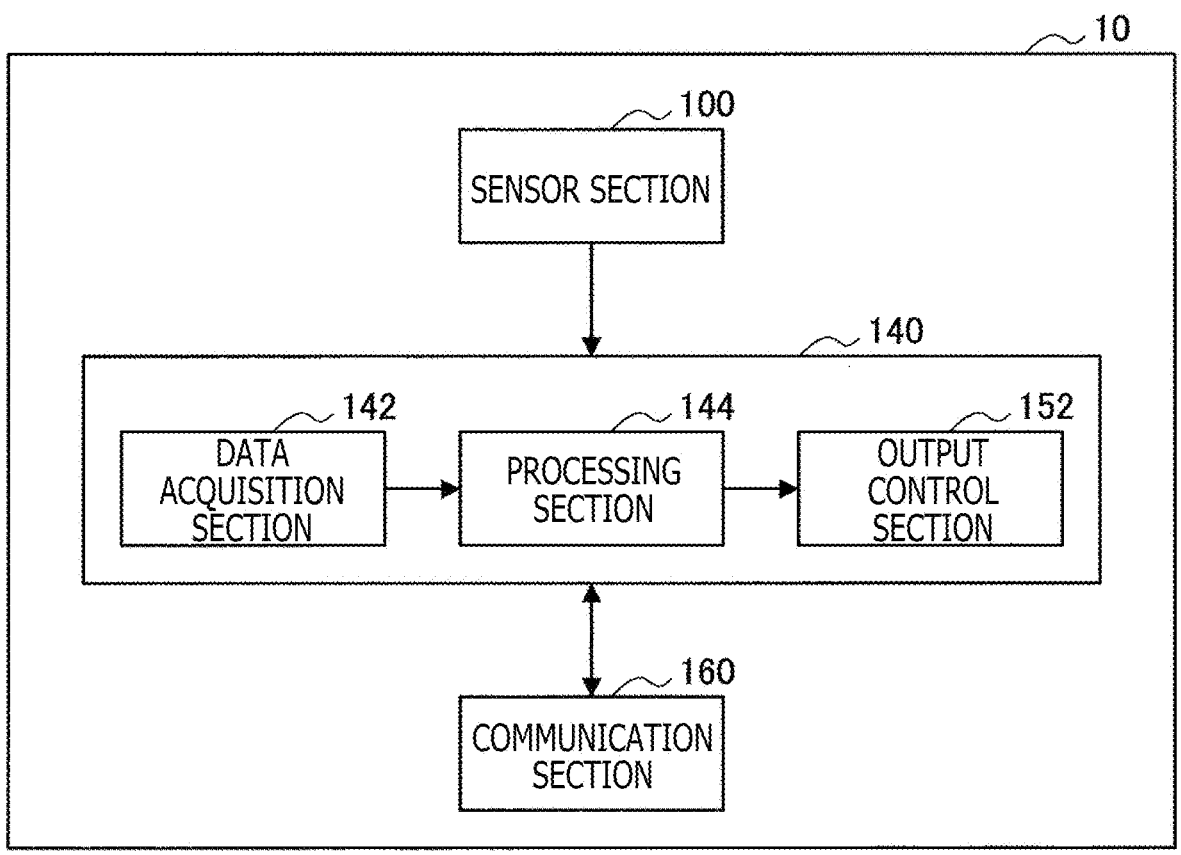
FIG. 2 is a block diagram depicting a configuration of a sensor apparatus 10 according to the embodiment of the present disclosure.

2.2. Configuration of Sensor Apparatus 10 According to Embodiment of Present Disclosure A configuration of the sensor apparatus 10 according to the embodiment of the present disclosure will next be described with reference to FIG. 2. FIG. 2 is a block diagram depicting the configuration of the sensor apparatus 10 according to the present embodiment. As depicted in FIG. 2, the sensor apparatus 10 according to the present embodiment mainly has a sensor section 100, a main control section 140, and a communication section 160. Details of the functional sections of the sensor apparatus 10 will be described hereinafter.

(Sensor Section 100)

The sensor section 100 can acquire, when attached to the body of the performer or the learner, the sensing data indicating a state of each motion element made by each part of the body of the learner or the performer during the performance. For example, the sensor section 100 is realized by one or a plurality of sensor devices including an acceleration sensor, an angular velocity sensor, a gyrosensor, a geomagnetic sensor, a position sensor, a vibration sensor, a pressure sensor, and a bending sensor. The sensor devices described above each detect changes in an acceleration, an angular velocity, or the like applied by the motion elements, and generate a plurality of pieces of sensing data indicating the detected changes. In a case in which the sensor section 100 is a sensor (first sensor) that acquires sensing data in an analog form, the sensing data is converted into sensing data in a digital form by a conversion apparatus (conversion section) 20 to be described later, and the sensing data in the digital form is output to the server 30. However, in the present embodiment, the sensor section 100 described above is not limited to a sensor that acquires sensing data in the analog form but may be a sensor (second sensor) that acquires sensing data in the digital form.

Moreover, the sensor section 100 may be, for example, a key touch detection sensor that detects vertical movements of keys of the piano (a subject) moving by a motion (performance) of the learner or the performer. It is possible to detect the vertical movement of each key by installing the key touch detection sensor, for example, below each key. Specifically, the sensor section 100 can be, for example, a pressure sensor that detects a pressure applied to each key of the piano by the motion element of the learner or the performer, or a photoreflector sensor including a light receiving/emitting sensor that detects the vertical movement of each key by reflection of light. It is noted that, in a case in which the sensor section 100 as described above is the sensor (first sensor) that acquires the sensing data in the analog form, the sensing data is converted into the sensing data in the digital form by the conversion apparatus 20, and the sensing data in the digital form is output to the server 30. Moreover, in the present embodiment, the subject for which detection is performed is not limited to the keys of the piano but may be another musical instrument (acoustic musical instrument or electronic musical instrument) per se or a part of the other musical instrument.

Furthermore, in the present embodiment, the sensor section 100 may be an imaging apparatus that images the learner or the performer, and in this case, it is possible to quantitatively detect positions and motions of joints of the performer or the like by causing a high speed imaging camera (imaging apparatus) to capture motions of the performer or the like. Moreover, in the present embodiment, the imaging apparatus may detect a motion of an eyeball (eyeball movement) or a size of a pupil (pupil diameter) of the learner or the performer. It is noted that, in the case in which the sensor section 100 as described above is the sensor (first sensor) that acquires the sensing data in the analog form, the sensing data is converted into the sensing data in the digital form by the conversion apparatus 20, and the sensing data in the digital form is output to the server 30, similarly to the description given so far.

Moreover, in the present embodiment, the sensor section 100 may be a nuclear magnetic resonance sensor that detects an oral cavity state or an intratracheal state, a motion of a lip or a tongue, and the like of the learner or the performer using nuclear magnetic resonance. Specifically, the sensor section 100 can detect the state, the motion, and the like described above by causing the learner or the like to execute a performance within an MRI (Magnetic Resonance Imaging) apparatus. Particularly in the case of applying the embodiment of the present disclosure to a playing technique for every type of brass instrument (a flute, an oboe, a clarinet, a trumpet, or the like), the MRI is useful since it is possible to detect the motion of the lip or the tongue that is difficult to detect by other methods. It is noted that, in the case in which the sensor section 100 as described above is the sensor (first sensor) that acquires the sensing data in the analog form, the sensing data is converted into the sensing data in the digital form by the conversion apparatus 20, and the sensing data in the digital form is output to the server 30, similarly to the description given so far.

Furthermore, in the present embodiment, the sensor section 100 may be a biological information sensor such as a myoelectric sensor, a heartbeat sensor, a pulse sensor, a blood flow sensor, a respiration sensor, a brain wave sensor, a skin temperature sensor, a skin electrical conductivity (skin resistance) sensor, or a perspiration sensor. It is noted herein that the myoelectric sensor is a sensor that senses a feeble electrical field generated from muscle fibers configuring muscles. More specifically, the myoelectric sensor can quantitatively detect muscle active masses of the muscles by measuring myoelectric potentials by electrical signals that are generated in muscle fibers when the muscles of an arm and the like of the performer or the learner contract and that are propagated through a surface of the body by a plurality of electrodes attached to the arm and the like. Furthermore, the heartbeat sensor is a sensor that detects a heartbeat that is a beat of a heart, and the pulse sensor is a sensor that detects a pulse that is an arterial pulsation appearing on the surface of the body or the like when pressure changes occur in artery linings by feeding a blood to an entire body through arteries. The blood flow sensor is a sensor that emits an infrared radiation to the body and that detects a blood flow rate by reflection of the infrared radiation. The respiration sensor can be a respiratory flowmeter that detects a change in a respiratory volume. The brain wave sensor is a sensor that detects a brain wave by attaching a plurality of electrodes to a scalp, removing noise from a fluctuation in a measured potential difference between the electrodes, and extracting a periodic wave. The skin temperature sensor is a sensor that detects a body temperature of the performer or the learner, and the skin electrical conductivity sensor is a sensor that detects a skin electrical resistance of the performer or the learner. Moreover, the perspiration sensor is a sensor that detects perspiration of the performer or the learner. It is noted that, in the case in which the sensor section 100 as described above is the sensor (first sensor) that acquires the sensing data in the analog form, the sensing data is converted into the sensing data in the digital form by the conversion apparatus 20, and the sensing data in the digital form is output to the server 30, similarly to the description given so far.

Furthermore, the sensor section 100 may be a sound pick-up apparatus that collects a sound from the piano played by the performer or the learner. The sensor section 100 may be, for example, a microphone provided in the vicinity of the piano. It is noted that, in the case in which the sensor section 100 as described above is the sensor (first sensor) that acquires the sensing data in the analog form, the sensing data is converted into the sensing data in the digital form by the conversion apparatus 20, and the sensing data in the digital form is output to the server 30, similarly to the description given so far.

Moreover, the sensing data from the sensor section 100 may be an output (sound data) from an electronic musical instrument played by the learner or the performer, that is, used in the performance. In other words, in the present embodiment, the sensor section 100 may be an electronic musical instrument. In this case, the sensing data from the sensor section 100 is data in the digital form compliant with, for example, a MIDI (Musical Instrument Digital Interface) standard.

Furthermore, the sensor section 100 may include a position information sensor such as a GPS (Global Positioning System) receiver or the like that acquires position information regarding the learner or the performer. In addition, the sensor section 100 may include other various types of sensors such as an atmospheric pressure sensor, a temperature sensor, and a humidity sensor for acquiring environmental information indicating a state of an environment where the learner or the performer gives the performance.

Moreover, in the present embodiment, the sensor section 100 may be every type of sensor already provided in a musical instrument (acoustic musical instrument or an electronic musical instrument) already shipped by each musical instrument manufacturer.

(Main Control Section 140)

The main control section 140 is provided in the sensor apparatus 10 and can exercise control over the blocks in the sensor apparatus 10. The main control section 140 is realized by hardware which is, for example, a CPU (Central Processing Unit), a ROM (Read Only Memory), and a RAM (Random Access Memory). Furthermore, the main control section 140 can function as a data acquisition section 142, a processing section 144, and an output control section 152. Details of these functional sections of the main control section 140 according to the present embodiment will be described hereinafter.

—Data Acquisition Section 142—

The data acquisition section 142 exercises control over the sensor section 100, acquires the sensing data output from the sensor section 100, and outputs the acquired sensing data to the processing section 144 to be described later.

—Processing Section 144—

The processing section 144 converts the sensing data output from the data acquisition section 142 described above into sensing data in a predetermined form in which the sensing data can be transmitted via the network 90, and outputs the sensing data in the predetermined form to the output control section 152 to be described later.

—Output Control Section 152—

The output control section 152 exercises control over the communication section 160 to be described later in such a manner as to transmit the sensing data in the predetermined form output from the processing section 144 described above to the server 30.

(Communication Section 160)

The communication section 160 is provided in the sensor apparatus 10, and can transmit and receive information to and from an external apparatus such as the server 30. In other words, the communication section 160 can be said as a communication interface having functions to transmit and receive data. It is noted that the communication section 160 is realized by communication devices such as a communication antenna, a transmitting-receiving circuit, and a port.

It is noted that the sensor apparatus 10 may be a wearable device of every type including the HMD type, the ear device type, the anklet type, the wristband type, the choker ring type, the eyewear type, the pad type, the badge type, a belt type, and the garment type. Specifically, these wearable devices can be provided, as motion capture devices, on a finger, an arm, a leg, the body, a head, and a toe of the learner or the performer in order to acquire various kinds of sensing data. Furthermore, the sensor apparatus 10 may be an apparatus, such as the imaging apparatus or the sound pick-up apparatus, installed around the learner or the performer, or may be the musical instrument per se used by the learner or the performer; thus, the sensor apparatus 10 is not limited to a specific type. Moreover, in the present embodiment, the sensor apparatus 10 is not limited to the configuration depicted in FIG. 2.

Figure 3:
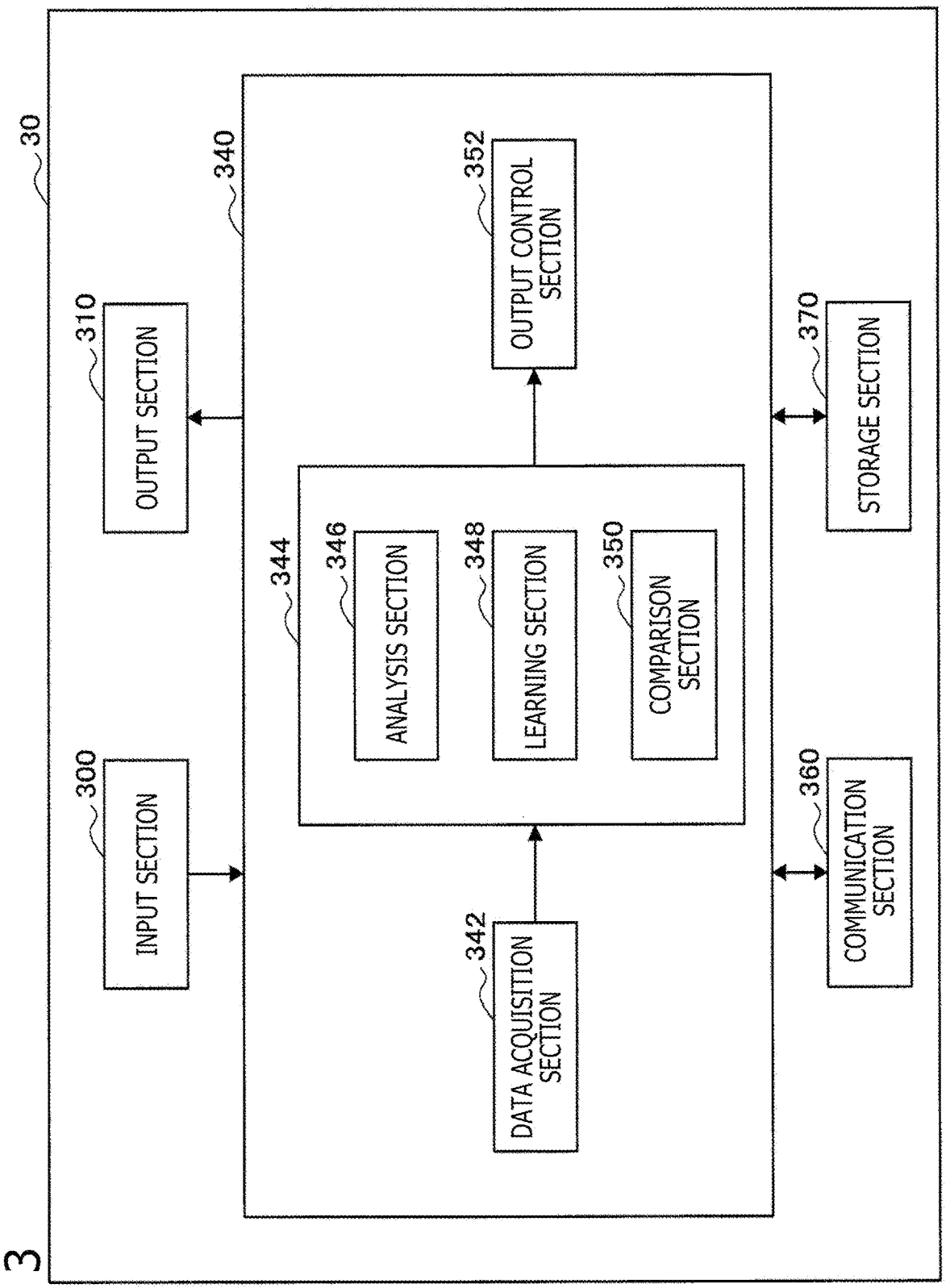
FIG. 3 is a block diagram depicting a configuration of a server 30 according to the embodiment of the present disclosure.

2.3. Configuration of Server 30 According to Embodiment of Present Disclosure A configuration of the server 30 according to the embodiment of the present disclosure will next be described with reference to FIG. 3. FIG. 3 is a block diagram depicting the configuration of the server 30 according to the embodiment of the present disclosure. As previously described, the server 30 is configured with, for example, a computer. As depicted in FIG. 3, the server 30 mainly has an input section 300, an output section 310, a main control section 340, a communication section 360, and a storage section 370. Details of the functional sections of the server 30 will be described hereinafter.

(Input Section 300)

The input section 300 receives inputs of data and commands transmitted to the server 30. More specifically, the input section 300 is realized by a touch panel, a keyboard, and the like, and can receive inputs of attribute information regarding the learner or the performer, subjective evaluations for the performance to be described later, and the like.

(Output Section 310)

The output section 310 is configured with, for example, a display, a speaker, a video output terminal, an audio output terminal, and the like, and outputs various types of information by images or audio.

(Main Control Section 340)

The main control section 340 is provided in the server 30 and can exercise control over the blocks in the server 30. The main control section 340 is realized by hardware which is, for example, a CPU, a ROM, and a RAM. Furthermore, the main control section 340 can function as a data acquisition section 342, an analysis section (information processing section) 346, and an output control section (information output section) 352. Details of these functional sections of the main control section 340 according to the present embodiment will be described hereinafter.

—Data Acquisition Section 342—

The data acquisition section 342 acquires the sensing data transmitted from the sensor apparatus 10 described above, and outputs the acquired sensing data to the processing section 344 to be described later.

—Processing Section 344—

The processing section 344 analyzes and processes the sensing data output from the data acquisition section 342 described above. The output control section 352 then generates feedback information to be fed back to the user on the basis of results of analysis and processing. Furthermore, the processing section 344 can construct a database (DB) 372 (refer to FIG. 10) including various types of information for generating the feedback information. More specifically, to realize these functions described above, the processing section 344 functions as an analysis section 346, a learning section 348, and a comparison section 350 as depicted in FIG. 3. Details of these functional sections of the processing section 344 according to the present embodiment will be described hereinafter.

The analysis section 346 performs analysis and the like on a plurality of pieces of sensing data that can be acquired in one trial, and extracts feature variables characterizing a state of the performance of the learner or the performer. The feature variables can be extracted as a maximum value, a minimum value, a mean value, an integral value, a period, an amount of change of each sensing data by statistically processing each sensing data by the analysis section 346. More specifically, the feature variables can be timings of peaks of muscle activities and maximum joint angles, and the like. The feature variables extracted in this way are linked to the plurality of pieces of sensing data acquired in the trial and stored in the storage section 370 to be described later as the DB 372. Furthermore, the analysis section 346 may output the extracted feature variables to the learning section 348, the comparison section 350, and the like to be described later.

Moreover, the analysis section 346 may perform analysis and the like on the plurality of pieces of sensing data (more specifically, for example, audio data related to the performance) that can be acquired in one trial, and extract evaluation values for the performance of the learner or the performer. The evaluation values are, for example, evaluation values for a piano performance, and can be the performance speed of the performer in the performance, the accuracy of the performance, the volume of the sound generated by the performance, the sound vibration, the timbre, the volume difference and the temporal difference among the musical tones in the chord, the difference between the maximum value and the minimum value of each sound parameter, the granularity of each sound parameter, and the like. The evaluation values extracted in this way are linked to the plurality of pieces of sensing data acquired in the trial and stored in the storage section 370 to be described later as the DB 372. Furthermore, the analysis section 346 may output the extracted evaluation values to the learning section 348, the comparison section 350, and the like to be described later.

The learning section 348 acquires information associated with relation among the sensing data, the feature variables, and the evaluation values by performing multivariate analysis thereon. More specifically, the learning section 348 is a supervised learning instrument such as a support vector regression and a deep neural network, and can perform machine learning on the relation between the sensing data and the evaluation values by performing, for example, the multivariate analysis such as multiple regression analysis thereon. Information regarding the relation (relation information) obtained by performing the machine learning by the learning section 348 can be stored in the storage section 370 to be described later as the DB 372, and can be used in selection of training data performed by the comparison section 350 to be described later.

The comparison section 350 selects one or a plurality of pieces of sensing data that serves as a model of the learner from the DB 372, and compares the selected sensing data (training data) with sensing data (comparison data) of the same item out of a plurality of pieces of newly acquired sensing data regarding the learner. More specifically, the comparison section 350 may calculate, for example, a difference (gap) between the training data and the comparison data or calculate a degree of matching of these pieces of data. Furthermore, the comparison section 350 may perform comparison by superimposing the training data on the comparison data.

Specifically, the comparison section 350 selects, as the training data, for example, representative sensing data that serves as the model of the learner aiming at an accurate performance from the DB 372, and compares the selected training data with the sensing data regarding the learner of the same item. At this time, in the case of presence of a plurality of pieces of representative sensing data serving as models, the comparison section 350 calculates a difference between each sensing data and the sensing data regarding the learner of the same item as an item of the representative sensing data. The comparison section 350 then selects the sensing data greatest in difference as the sensing data related to an element with high necessity of correction such that the performance of the learner becomes more accurate. In the present embodiment, such selection makes it possible to pay more attention on a technical element which the learner is slowest in learning; thus, it is possible to generate the feedback information useful to efficiently acquire the accurate performance.

Alternatively, the comparison section 350 may select, as the training data, the sensing data estimated to have a higher relation with the accuracy (evaluation value) of the performance on the basis of the information regarding the relation obtained by the learning section 348 described above. In the present embodiment, such selection makes it possible to pay more attention on a technical element that enables efficient acquisition of the accurate performance; thus, it is possible to generate the feedback information useful to efficiently acquire the accurate performance.

In another alternative, in the present embodiment, the comparison section 350 may select, as the training data, the sensing data related to a performer having the same or similar attribute information as or to attribute information (a gender, an age, a physical size, a muscle force, tenderness, legerity, and the like) regarding the learner on the basis of the attribute information regarding the learner. In the present embodiment, such selection makes it possible to perform feedback tailormade to attributes and the like of the learner; thus, the learner can efficiently perform learning. Moreover, in the case of comparison between a past state and a current state of the performance of the learner, the comparison section 350 may select past sensing data regarding the learner.

Moreover, in the present embodiment, the comparison section 350 is not limited to comparing the sensing data but may compare the feature variables extracted by the analysis section 346 described above. Even in such a case, the comparison section 350 can perform the selection described above in a case in which a plurality of representative feature variables serving as models is present.

—Output Control Section 352—

The output control section 352 generates the feedback information on the basis of a result of comparison by the comparison section 350, and exercises control over the communication section 360 to be described later in such a manner as to transmit the feedback information to the feedback apparatus 70. The transmitted feedback information is output to the user via the feedback apparatus 70. Furthermore, the output control section 352 may perform processing for emphasizing or reducing the difference (gap) between the training data and the comparison data by expanding or contracting the difference either spatially or temporally, and generate the feedback information. Specifically, in the present embodiment, the output control section 352 feeds back the feedback information generated by reducing the difference to the learner at a technical level greater in difference from the training data to avoid decrease of motivation of learning. On the other hand, in the present embodiment, the output control section 352 feeds back the feedback information generated by emphasizing the small difference to guide the learner to a higher technical level in such a manner that the learner can easily recognize the difference, to the learner at the technical level smaller in difference from that of the training data. In other words, in the present embodiment, performing the processing as described above makes it possible for the learner to easily recognize the difference from the training data while avoiding the decrease of the motivation of the learner; thus, it is possible to realize assistance of efficient learning of the performance.

Moreover, the output control section 352 may select a sensation modality (such as a visual sensation, an auditory sensation, or a tactile sensation) suited for the feedback information on the basis of user's situations and the like, and transmit the feedback information to the feedback apparatus 70 according to the selected sensation modality. In the present embodiment, the feedback information can be provided to the user by the sensation modality according to the user's situations and the like; thus, it is possible to realize assistance of efficient learning of the performance.

(Communication Section 360)

The communication section 360 is provided in the server 30, and can transmit and receive information to and from an external apparatus such as the sensor apparatus 10 or the feedback apparatus 70. It is noted that the communication section 360 is realized by communication devices such as a communication antenna, a transmitting-receiving circuit, and a port.

(Storage Section 370)

The storage section 370 is provided in the server 30 and stores therein programs, information, and the like for the main control section 340 described above to execute various types of processing. Furthermore, the storage section 370 stores therein the DB 372 including the plurality of pieces of sensing data linked to various types of attribute information and the like (a metafile). It is noted that the storage section 370 is realized by a magnetic recording medium such as a hard disk (HD), a nonvolatile memory such as a flash memory, or the like.

It is noted that the metafile (attribute information) can contain attribute information associated with the learner or the performer (the name, the gender, the age, a body height, a body weight, the physical size, the muscle force, a palm size, the tenderness, the legerity, years of experience of piano playing, a skill level, a national origin, an instructor name, and the like), attribute information associated with the performance (date and time of performance, a title of a music, a category of the music, a name of a composer, an epoch of composition, a category of the composer, a tempo, a volume, information whether a single tone or complexed tones, contents of teaching given to the performer or the learner, the musical instrument for the performance, a location of the performance, and the like), feature variables characterizing the performance, evaluation values (evaluation information) for the performance, attribute information associated with sensing (a sensor type, a sampling frequency, the number of channels, and the like), sensitivity evaluation information regarding the performance (information such as an image, a timbre, and a vibration the performer is to express), and the like. The metafile can also contain attribute information regarding each trial (a competition name, a competition level, an attendance, the number of fans, evaluation information regarding attendance, the number of views, and the like). In other words, the metafile functions as a label of the plurality of pieces of sensing data (sensing data group) acquired in one trial, and can indicate, for example, that the sensing data group is information sensed when a certain performer performs a certain piece while aiming to express the piece in a certain manner.

Furthermore, in the present embodiment, the server 30 is not limited to the configuration depicted in FIG. 3 but may include other functional blocks and the like.

2.4. Configurations of Conversion Apparatus 20 and Computing Apparatus 26 According to Embodiment of Present Disclosure Meanwhile, as previously described, the sensing data obtained by the sensor apparatus 10 included in the information processing system 1 according to the present embodiment is a mixture of the sensing data in the analog form and the sensing data in the digital form. To acquire data useful for assistance of learning of the performance of the learner, it is required to accurately synchronize a plurality of pieces of sensing data even in a mixture of forms described above.

Figure 4:
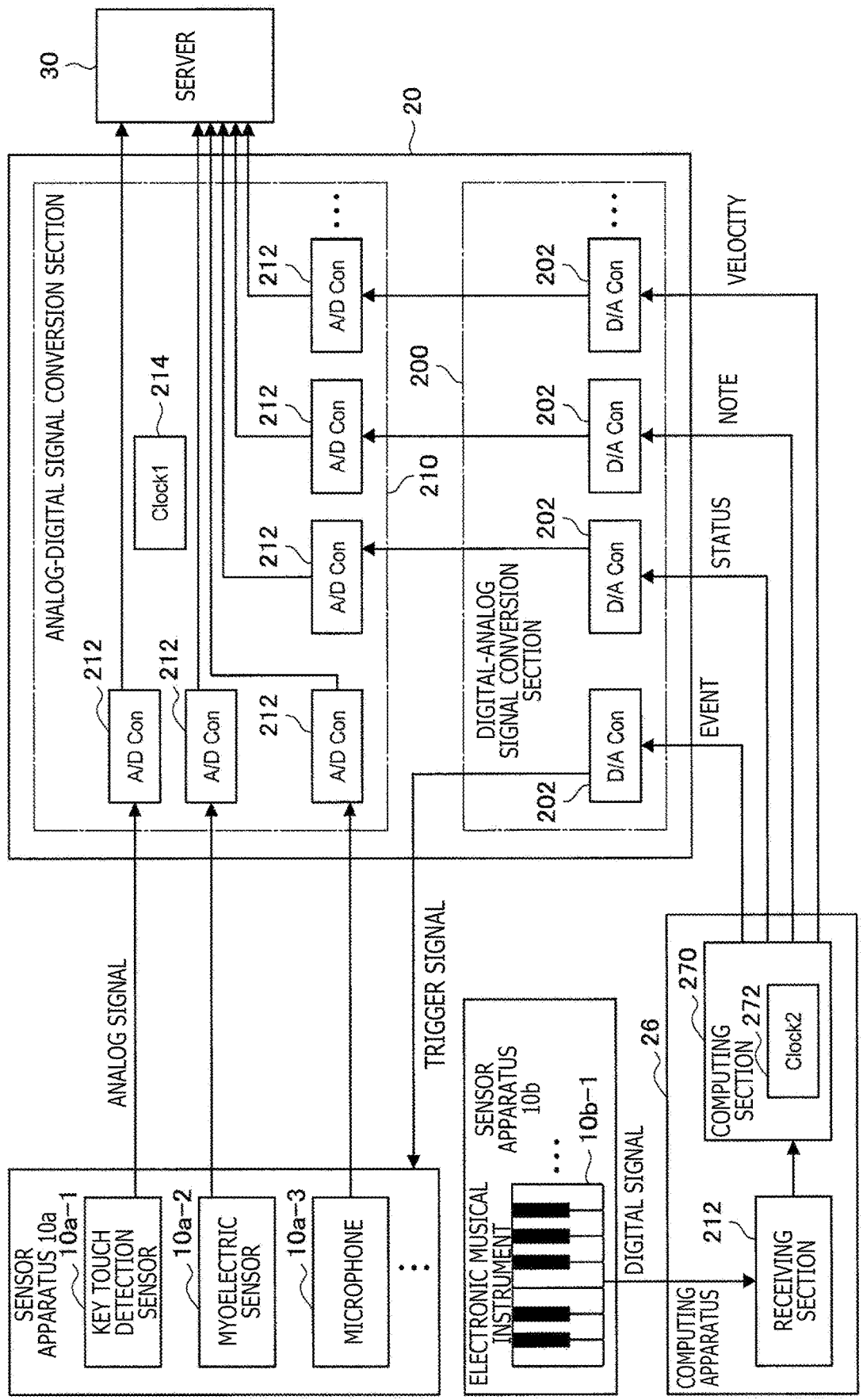
FIG. 4 is a block diagram depicting configurations of a conversion apparatus 20 and a computing apparatus 26 according to the embodiment of the present disclosure.

In the present embodiment, therefore, it is preferable to provide the conversion apparatus (conversion section) 20 and a computing apparatus 26 between the sensor apparatus 10 and the server 30 as depicted in FIG. 4. Therefore, the conversion apparatus 20 and the computing apparatus 26 according to the present embodiment will be described hereinafter with reference to FIG. 4. FIG. 4 is a block diagram depicting configurations of the conversion apparatus 20 and the computing apparatus 26 according to the present embodiment. More specifically, the information processing system 1 according to the present embodiment includes the conversion apparatus 20 and the computing apparatus 26 as depicted in FIG. 4 between the sensor apparatus 10 and the server 30. Details of the conversion apparatus 20 and the computing apparatus 26 will be described hereinafter.

(Conversion Apparatus 20)

As depicted in FIG. 4, the conversion apparatus 20 is an apparatus that converts a plurality of pieces of sensing data in different forms obtained from a plurality of sensor apparatuses 10, and mainly has a digital-analog signal conversion section 200 and an analog-digital signal conversion section 210. Details of the digital-analog signal conversion section 200 and the analog-digital signal conversion section 210 of the conversion apparatus 20 will be described hereinafter.

—Digital-Analog Signal Conversion Section 200—

The digital-analog signal conversion section 200 converts sensing data received from a sensor apparatus (second sensor) 10*b* that outputs sensing data in the digital form among the plurality of sensor apparatuses 10 via the computing apparatus 26, to be described later, into sensing data in the analog form. Furthermore, the digital-analog signal conversion section 200 outputs the sensing data in the analog form obtained by conversion to the analog-digital signal conversion section 210 to be described later.

More specifically, the digital-analog signal conversion section 200 has a plurality of digital-analog converters (D/A converters) 202 including a microcomputer board and the like. For example, one sensing data acquired by one sensor apparatus 10*b* is extracted as sensing data in one of a plurality of channels by the computing apparatus 26 to be described later. The extracted sensing data per channel is input to each of the D/A converters 202. Specifically, in a case in which the sensor apparatus 10*b* is an electronic piano that outputs a MIDI signal that is sensing data in the digital form compliant with the MIDI standard, each packet in the MIDI signal contains information regarding an event such as key touch/key release (a status), information regarding a pitch of a generated sound (a note), and information regarding a loudness of the sound (a velocity). In the present embodiment, therefore, the computing apparatus 26 extracts the MIDI signal as pieces of sensing data regarding the status, the note, and the velocity as described above per channel, and inputs the extracted sensing data to the D/A converters 202. Moreover, each extracted sensing data is converted into sensing data in the analog form by each D/A converter 202, and the sensing data in the analog form is input to the analog-digital signal conversion section 210 to be described later. In the embodiment, converting the sensing data in the digital form into the sensing data in the analog form in this way makes it possible to simultaneously handle the sensing data in the analog form with the sensing data that is in the analog form from the first start and that is output from a sensor apparatus 10*a*.

Moreover, a part of the sensing data the form of which is converted into the analog form by the digital-analog signal conversion section 200 contains, for example, information regarding a timing of occurrence of an event such as a moment of touching specific keys at a strength equal to or higher than a certain level (event). Therefore, sensing data containing such an event may be converted into sensing data in the analog form by the digital-analog signal conversion section 200, and input to the other sensor apparatus 10 (for example, the sensor apparatus (first sensor) 10*a* that acquires the sensing data in the analog form) as a trigger signal. The trigger signal can be used for the sensor apparatus 10*a* to start (drive) acquiring the sensing data.

—Analog-Digital Signal Conversion Section 210—

The analog-digital signal conversion section 210 converts sensing data from the sensor apparatus (first sensor) 10*a* that outputs sensing data in the analog form among the plurality of sensor apparatuses 10 into sensing data in the digital form. Furthermore, the analog-digital signal conversion section 210 converts the sensing data in the analog form into which the digital-analog signal conversion section 200 described above converts the sensing data in the digital form, into sensing data in the digital form. The analog-digital signal conversion section 210 then outputs the sensing data obtained by conversion to the server 30 described above. More specifically, the analog-digital signal conversion section 210 has a plurality of analog-digital converters (A/D converters) 212 including a microcomputer board and the like, and each A/D converter 212 can convert each sensing data in the analog form into the sensing data in the digital form and output the sensing data in the digital form to the server 30.

Furthermore, the analog-digital signal conversion section 210 has a clock (first clock mechanism) 214 mounted on the microcomputer board to synchronize a plurality of pieces of sensing data. The clock 214 simultaneously outputs a trigger signal to each of the A/D converters 212 or each sensor apparatus 10*a*, and causes the A/D converter 212 or the sensor apparatus 10*a* to start acquiring the sensing data by the trigger signal, thereby making it possible to match timings of acquiring the sensing data. In other words, in the present embodiment, the clock 214 enables the pieces of sensing data from the plurality of sensing apparatuses 10*a* to be accurately synchronized with one another. It is noted that the clock 214 may output clock time information to the server 30.

(Computing Apparatus 26)

The computing apparatus 26 acquires the sensing data from the sensor apparatus 10*b* that acquires the sensing data in the digital form, and extracts the acquired sensing data as sensing data per channel (containing, for example, the status, the note, and the velocity). Furthermore, the computing apparatus 26 outputs the sensing data extracted for each of a plurality of channels to the conversion apparatus 20 described above. More specifically, the computing apparatus 26 mainly has a receiving section 260 and a computing section 270 as depicted in FIG. 4. Details of the receiving section 260 and the computing section 270 of the computing apparatus 26 will be described hereinafter.

—Receiving Section 260—

The receiving section 260 receives the sensing data from the sensor apparatus 10*b* that acquires the sensing data in the digital form, and outputs the sensing data in the digital form to the computing section 270 to be described later.

—Computing Section 270—

The computing section 270 extracts the sensing data acquired from the receiving section 260 described above as the sensing data per channel. For example, as described above, the computing section 270 extracts the status, the note, and the velocity contained in each packet in the MIDI signal that is the sensing data in the digital form as the sensing data per channel. Furthermore, the computing section 270 outputs the extracted sensing data per channel to the conversion apparatus 20 described above.

Furthermore, the computing section 270 may have a clock (second clock mechanism) 272 mounted on a microcomputer board to synchronize the plurality of pieces of sensing data. The clock 272 can link clock time information to the sensing data. In the present embodiment, since the clock 272 links the sensing data in the plurality of channels from the sensor apparatus 10b to the same clock time information, it is possible to match clock times of the pieces of sensing data with one another, that is, it is possible to synchronize the pieces of sensing data. It is noted that the clock 272 may output the clock time information to the server 30.

Furthermore, the server 30 can synchronize the plurality of pieces of sensing data from the conversion apparatus 20 on the basis of the clock time information from the clocks 214 and 272. More specifically, the sensing data from the sensor apparatus 10b that acquires the sensing data in the digital form is converted into the sensing data in the analog form in advance, and then the sensing data in the analog form is converted into the sensing data in the digital form. On the other hand, the sensing data from the sensor apparatus 10a that acquires the sensing data in the analog form is converted into the sensing data in the digital form without being converted into the sensing data in the analog form in advance. Therefore, a minor temporal difference is generated between the sensing data from the sensor apparatus 10b and the sensing data from the sensor apparatus 10a at a point in time of arrival of the sensing data at the server 30. In the present embodiment, therefore, to accurately synchronize the sensing data from the sensor apparatus 10b with the sensing data from the sensor apparatus 10a, the server 30 performs temporal shift processing on these pieces of sensing data on the basis of a temporal difference between the clocks 214 and 272 obtained from the clock time information. According to the present embodiment, therefore, it is possible to match time bases for the plurality of pieces of sensing data in a mixture of forms and accurately synchronize and handle these pieces of sensing data.

It is noted that the clock 272 is not necessarily provided in the computing apparatus 26 and may be provided in the sensor apparatus 10b or in a portion of the digital-analog signal conversion section 200 closer to the computing apparatus 26, that is, closer to the sensor apparatus 10b.

It is noted that, in the present embodiment, the configurations of the conversion apparatus 20 and the computing apparatus 26 are not limited to those depicted in FIG. 4. For example, both or one of the conversion apparatus 20 or the computing apparatus 26 may be provided in the server 30 described above. Alternatively, the conversion apparatus 20 may be provided in the sensor apparatus 10a, or the computing apparatus 26 may be provided in the sensor apparatus 10b; thus, the configurations of the conversion apparatus 20 and the computing apparatus 26 are not limited to specific ones. Nevertheless, providing any one of the conversion apparatus 20 or the computing apparatus 26 in the sensor apparatus 10a or 10b means that a weight of the sensor apparatus 10 attached to the body of the performer or the learner or attached to the subject moving according to the motion of the performer or the learner becomes heavier. In addition, it is estimated that the weight has an influence on the performance of the performer or the learner. Moreover, in such a case, it is estimated that the sensing data from the sensor apparatuses 10a and 10b tend to contain noise. It is, therefore, preferable that the conversion apparatus 20 and the computing apparatus 26 are provided in locations other than the sensor apparatuses 10a and 10b to avoid the influence on the performance and the noise.

As described so far, by having the conversion apparatus 20 described above, the information processing system 1 according to the present embodiment can accurately synchronize the pieces of sensing data even in the case of a mixture of the sensing data in the analog form and the sensing data in the digital form. As a result, the information processing system 1 can simultaneously analyze the plurality of pieces of sensing data accurately synchronized with one another and containing various information; thus, it is possible to acquire data useful for assistance of learning of the performance of the learner.

Figure 5:
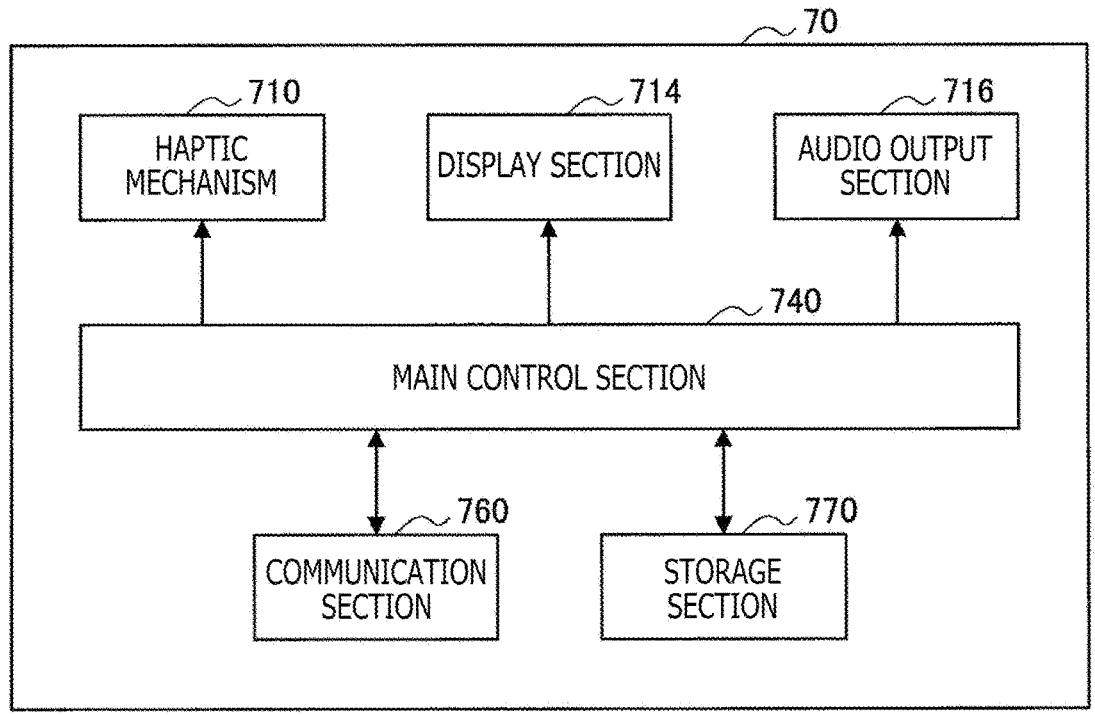
FIG. 5 is a block diagram depicting a configuration of a feedback apparatus 70 according to the embodiment of the present disclosure.

2.5. Configuration of Feedback Apparatus 70 According to Embodiment of Present Disclosure A configuration of the feedback apparatus 70 according to the embodiment of the present disclosure will next be described with reference to FIG. 5. FIG. 5 is a block diagram depicting the configuration of the feedback apparatus 70 according to the present embodiment. As previously described, the feedback apparatus 70 can be a device such as the tablet, the laptop PC, the notebook PC, or the wearable device. Furthermore, as depicted in FIG. 5, the feedback apparatus 70 mainly has a haptic mechanism 710, a display section 714, an audio output section 716, a main control section 740, a communication section 760, and a storage section 770. Details of the functional sections of the feedback apparatus 70 will be described hereinafter.

(Haptic Mechanism 710)

The haptic mechanism 710 is an apparatus that propagates a sense of force (tactile sensation), for example, applies a force to a part (for example, a joint) of the body of the learner on the basis of the feedback information transmitted from the server 30. For example, the haptic mechanism can be a glove type wearable device (wearable apparatus) attached to a hand of the learner. Furthermore, in the present embodiment, the haptic mechanism 710 is not limited to the glove type wearable device and may be, for example, a vibration apparatus that applies a vibration to a part of the body of the learner or a stimulation apparatus that uses electrical muscle stimulation to give a stimulus to muscles. In other words, in the present embodiment, it is sufficient if the haptic mechanism 710 is capable of sensorily feeding back the feedback information to the learner (performing bio-feedback) by giving a tactile stimulus to a part of the body of the learner.

(Display Section 714)

The display section 714 is a device for displaying the feedback information to the user, and outputs the feedback information toward the user by, for example, images or light. The display section 714 is realized by, for example, a display, a light-emitting element (not depicted), and the like. Furthermore, the display section 714 may be realized by a video output terminal and the like.

Moreover, the display section 714 may be a projection apparatus that can display an object based on feedback information 610 by superimposing the object onto a real space as augmented reality (AR). Such a projection apparatus can be, for example, a smart glass type wearable device attached in front of learner's eyes. A transmissive display is provided in the smart glass type wearable device, and the transmissive display holds a virtual image optical system including a transparent light guide section and the like in front of the learner's eyes using, for example, a half-mirror and a transparent light guide plate, and displays the object inside of the virtual image optical system. Furthermore, the projection apparatus may be an HMD attached to the learner's head.

(Audio Output Section 716)

The audio output section 716 is a device that outputs the feedback information to the user as audio, and may be, for example, a headphone speaker attached to a learner's ear or a speaker (not depicted) provided in the vicinity of the learner. Furthermore, the audio output section 716 may be realized by an audio output terminal and the like.

In this way, in the present embodiment, means corresponding to a suited sensation modality is selected from among the haptic mechanism 710, the display section 714, and the audio output section 716 according to the feedback information and the like and the user's situations and the like, and the feedback information can be fed back to the learner or the like. Moreover, in the present embodiment, the haptic mechanism 710, the display section 714, and the audio output section 716 may simultaneously perform feedback by a plurality of sensation modalities, and a method of the feedback is not limited to a specific method.

(Main Control Section 740)

The main control section 740 is provided in the feedback apparatus 70 and can exercise control over the blocks in the feedback apparatus 70. The main control section 740 is realized by hardware which is, for example, a CPU, a ROM, and a RAM.

(Communication Section 760)

The communication section 760 can transmit and receive information to and from an external apparatus such as the server 30. It is noted that the communication section 760 is realized by communication devices such as a communication antenna, a transmitting-receiving circuit, and a port.

(Storage Section 770)

The storage section 770 is provided in the feedback apparatus 70, and stores therein programs and the like for the main control section 740 to execute various types of processing and information obtained by the processing. It is noted that the storage section 770 is realized by a magnetic recording medium such as an HD, a nonvolatile memory such as a flash memory, or the like.

Moreover, the feedback apparatus 70 may have an input section that is not depicted. The input section has a function to receive input of data and commands transmitted to the feedback apparatus 70. More specifically, the input section is realized by a touch panel, buttons, switches, keys, a keyboard, a microphone, an image sensor, and the like Furthermore, in the present embodiment, a function of the sensor section 100 in the sensor apparatus 10 and the haptic mechanism 710 and the like in the feedback apparatus 70 may be integrated into one wearable device. It is noted that, in the present embodiment, the feedback apparatus 70 is not limited to the configuration depicted in FIG. 5 and may have, for example, other functional sections.

Figure 6:
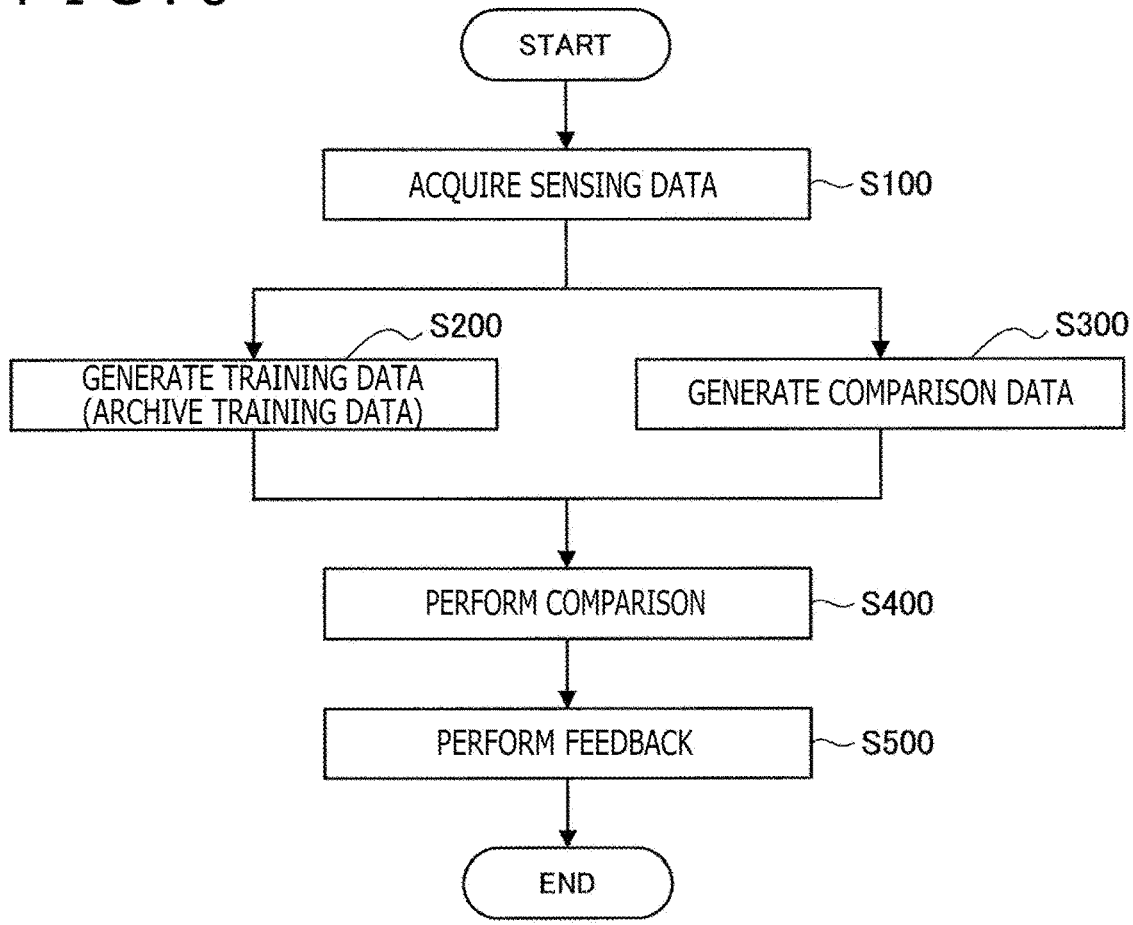
FIG. 6 is a flowchart illustrating an example of an information processing method according to the embodiment of the present disclosure.

2.6. Information Processing Method According to Embodiment of Present Disclosure The configuration of the information processing system 1 according to the present embodiment and those of the apparatuses included in the information processing system 1 have been described so far in detail. An information processing method according to the present embodiment will next be described with reference to FIG. 6. FIG. 6 is a flowchart illustrating an example of the information processing method according to the present embodiment.

As depicted in FIG. 6, the information processing method according to the present embodiment includes a plurality of steps from Step S100 to Step S500. Details of the steps included in the information processing method according to the present embodiment will be described hereinafter.

(Step S100)

First, the sensor apparatus 10 is attached to a part of the body of the learner or the performer in advance or installed around the learner or the like before the performance of the learner or the like. When the learner or the like then starts a predetermined performance (such as a piece of music, a phrase, a scale, an arpeggio, or a chord) as a trial, the sensor section 100 of the sensor apparatus 10 senses movements of the body, the musical instrument, and the like generated to accompany the performance (motion) of the learner or the like during the performance, a sound generated by the musical instrument, and the like, and acquires a plurality of pieces of sensing data. Furthermore, the sensor apparatus 10 outputs the acquired sensing data to the server 30.

At this time, the sensing data acquired by the sensor apparatus 10 is converted by the conversion apparatus 20 described above and the converted sensing data is input to the server 30. In the information processing system 1 according to the present embodiment, therefore, the conversion apparatus 20 can accurately synchronize the pieces of sensing data even in the case of the mixture of the sensing data in the analog form and the sensing data in the digital form, as previously described. As a result, the server 30 can simultaneously analyze the plurality of pieces of sensing data accurately synchronized and containing various types of information in a subsequently executed step; thus, it is possible to acquire data useful for assistance of the learning of the performance of the learner.

In the present embodiment, it is preferable to allow many performers (for example, approximately 100 performers) to each give a predetermined performance (such as a piece of music, a phrase, a scale, an arpeggio, or a chord) and to collect many pieces of sensing data to acquire information for constructing the DB 372. Furthermore, at that time, the server 30 may acquire the attribute information associated with each performer (the gender, the age, the body height, the body weight, the physical size, the muscle force, the palm size, the tenderness, the legerity, the years of experience of piano playing, the skill level, and the like) and the attribute information associated with the performance (the date and time, the title of music, the name of a composer, the musical instrument for the performance, the location of the performance, and the like).

(Step S200)

The server 30 generates training data on the basis of the sensing data regarding the performer acquired in Step S100. The generated training data is stored (archived) as the DB 372. It is noted that details of Step S200 will be described later.

(Step S300)

The server 30 generates comparison data on the basis of the sensing data regarding the learner acquired in Step S100. The generated comparison data may be stored as the DB 372. It is noted that details of Step S300 will be described later.

(Step S400)

The server 30 selects the training data from the DB 372 and compares the selected training data with the comparison data generated in Step S300 described above. The server 30 then generates feedback information to be fed back to the learner on the basis of a comparison result. It is noted that details of Step S400 will be described later.
(Step S500)

The feedback apparatus 70 performs feedback to the learner on the basis of the feedback information generated in Step S400 described above.

The details of Steps S200, S300, and S400 depicted in FIG. 6 will be described hereinafter.

(2.6.1 Details of Creation of Training Data)

Figure 7:
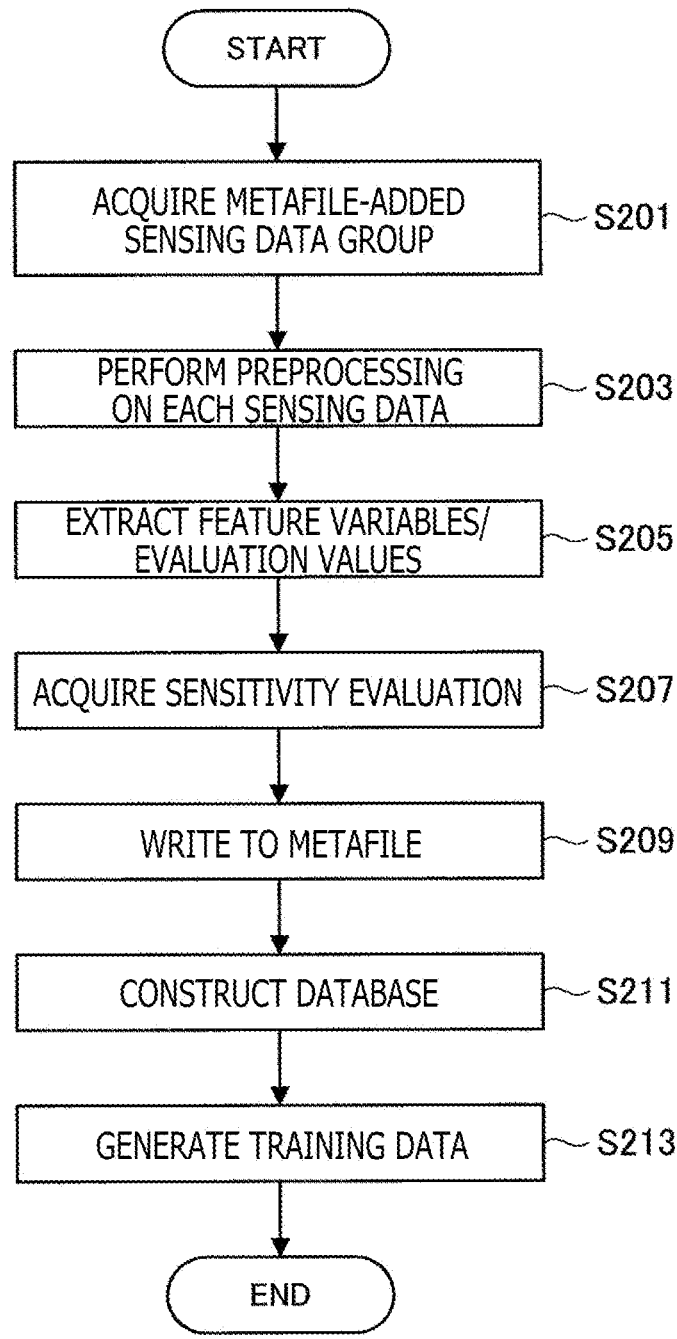
FIG. 7 is a flowchart of creating training data according to the embodiment of the present disclosure.
Figure 8:
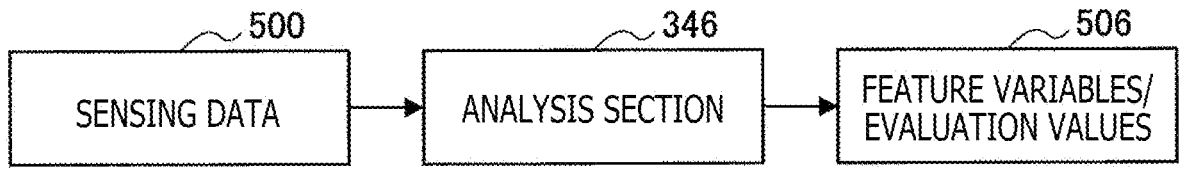
FIG. 8 is an explanatory diagram (1) of an example of extraction of feature variables.
Figure 9:
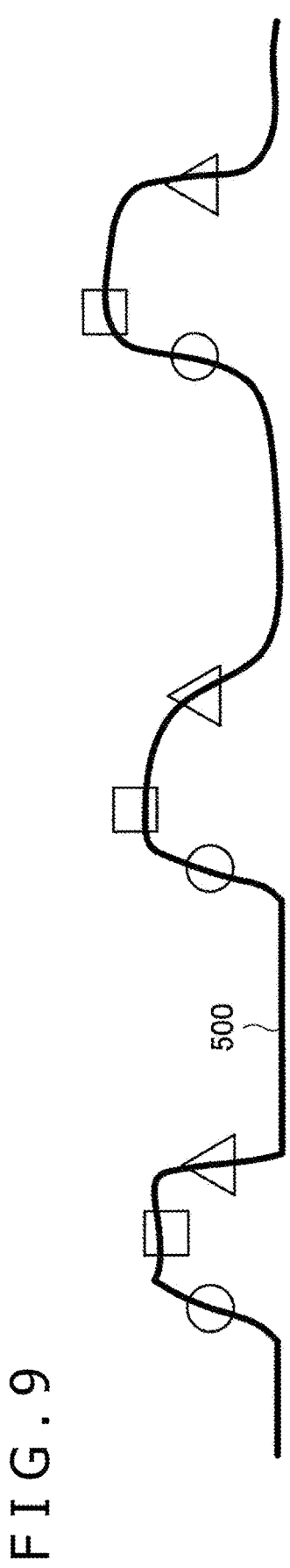
FIG. 9 is an explanatory diagram (2) of the example of extraction of feature variables.
Figure 10:
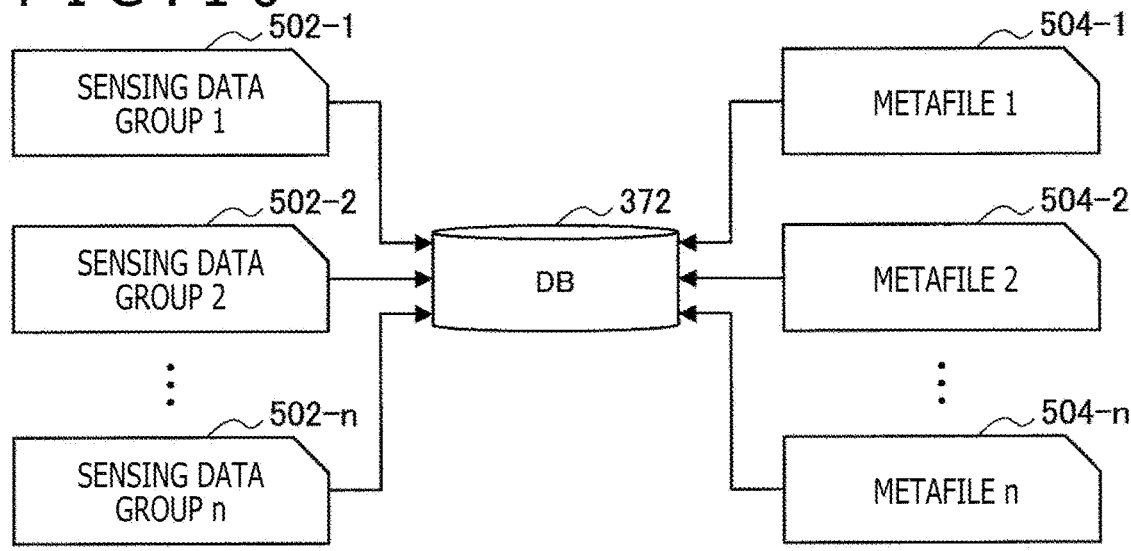
FIG. 10 is an explanatory diagram (1) of an example of constructing a database.
Figure 11:
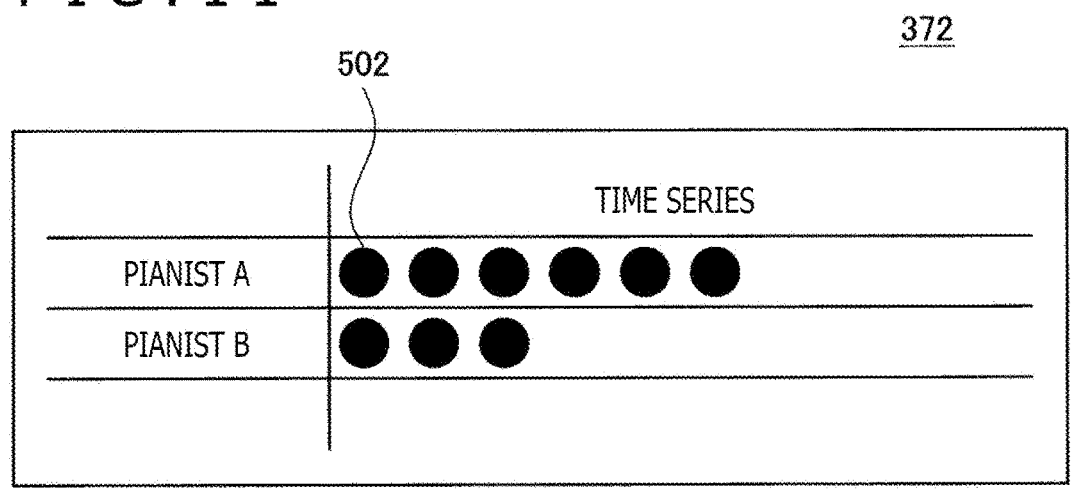
FIG. 11 is an explanatory diagram (2) of the example of constructing a database.
Figure 12:
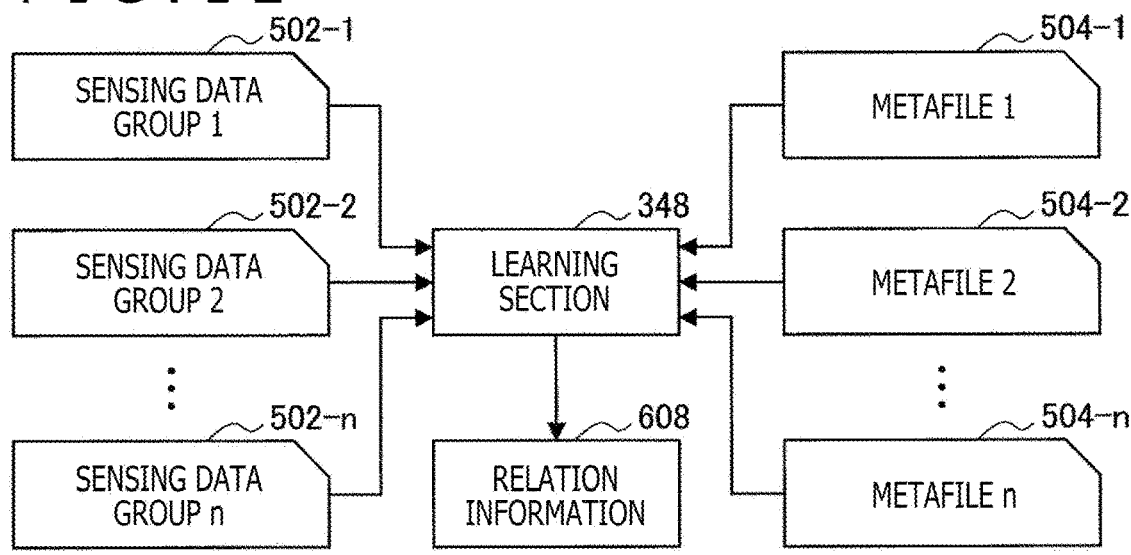
FIG. 12 is an explanatory diagram (1) of an example of creating training data.

First, details of creation of the training data in Step S200 of FIG. 6 described above will be described with reference to FIGS. 7 to 13. FIG. 7 is a flowchart of creating the training data according to the present embodiment. FIGS. 8 and 9 are explanatory diagrams of an example of extraction of feature variables 506. Furthermore, FIGS. 10 and 11 are explanatory diagrams of an example of construction of the database 372, and FIGS. 12 and 13 are explanatory diagrams of an example of creation of the training data.

As depicted in FIG. 7, the creation of the training data includes a plurality of steps from Step S201 to Step S213. Details of these plurality of steps will be described hereinafter.

(Step S201)

The server 30 acquires the plurality of pieces of sensing data (a sensing data group) acquired by each sensor apparatus 10 as one text file from start until end of sensing in one trial. A metafile is linked to the text file, and the metafile can contain the attribute information associated with the performer, the attribute information associated with the performance, and the like, as previously described. The metafile can also contain the attribute information regarding the trial (the competition name, the competition level, the attendance, the number of fans, the evaluation information regarding attendance, the number of views, and the like). In the present embodiment, linking the metafile to the sensing data group in this way makes it possible to appropriately and easily manage the sensing data group and select the training data by referring to various types of information contained in the metafile.

It is noted that the above information contained in the metafile may be input by the user to the server 30, or may be generated by analyzing the sensing data and automatically extracting the information if the information can be analyzed from the sensing data. For example, a piece performed may be automatically extracted and the attendance present in the surroundings may be estimated by analyzing the sound information contained in the sensing data, and the location of the performance may be automatically extracted by analyzing the position information contained in the sensing data.

(Step S203)

The server 30 removes noise and the like contained in each sensing data acquired in Step S201 by performing filtering and statistical processing (abnormal value detection) (preprocessing).

(Step S205)

The server 30 performs analysis and the like on the plurality of pieces of sensing data acquired in one trial and preprocessed in Step S203 described above, and extracts feature variables characterizing the state of the performance. The feature variables extracted in this way are written to the metafile in Step S209 to be described later. Specifically, the analysis section 346 of the server 30 analyzes sensing data 500 and extracts feature variables 506, as depicted in FIG. 8. For example, the feature variables 506 can be extracted as the maximum value, the minimum value, the mean value, the integral value, the period, and the amount of change of each of the sensing data 500 by statistically processing the sensing data 500 by the analysis section 346. More specifically, as the feature variables 506, timings at which the keys are located at uppermost positions, timings at which a key touch ascent velocity becomes maximum, and timings at which a key touch descent velocity becomes maximum, as indicated by white circle, white triangle, and white rectangle markers, are extracted on the sensing data 500 that is time-series data regarding moving amounts of the keys depicted in FIG. 9.

As depicted in FIG. 8, the analysis section 346 of the server 30 may perform analysis and the like on the plurality of pieces of sensing data (for example, audio data related to the performance) 500 acquired in one trial and preprocessed in Step S203 as described above, and extract evaluation values 506a for the performance. The evaluation values 506a can be the performance speed of the performer in the performance, the accuracy of the performance, the volume of the sound generated by the performance, the sound vibration, the timbre, the volume difference and the temporal difference among the musical tones in the chord, the difference between the maximum value and the minimum value of each sound parameter, the granularity of each sound parameter, and the like, as previously described. The evaluation values 506a extracted in this way are written to the metafile in Step S209 to be described later, similarly to the feature variables 506.

(Step S207)

Furthermore, the server 30 acquires information regarding a sensitivity evaluation that is an evaluation of sensitivity for the performance that cannot be directly evaluated by the feature variables 506 and the evaluation values 506a described above. For example, the server 30 acquires the sensitivity evaluation by causing the performer to input the sensitivity for the own performance (brilliant, flowing, heavy, surrounding, lyrical, soft, hard, or the like) after end of the trial. The acquired sensitivity evaluation is written to the metafile in Step S209 to be described later, similarly to the feature variables 506. It is noted that a method of acquiring the information regarding the sensitivity evaluation is not limited to the method by causing the performer to directly input the sensitivity, but the information regarding the sensitivity evaluation may be automatically acquired by audio analysis of murmurs or the like of the performer during the performance. In the present embodiment, automatically acquiring the information regarding the sensitivity evaluation by the audio analysis in this way makes it possible to acquire the information regarding the sensitivity evaluation without bothering the performer.

Moreover, in the present embodiment, the information regarding the sensitivity evaluation may be acquired by other methods. For example, many people (for example, professionals such as pianists and nonprofessionals other than the professionals) are asked to listen to various types of music (for example, performances of performers and performances of nonprofessionals, not limited to specific performances) in advance and to perform the sensitivity evaluation for each piece of music. Next, the server 30 inputs the sensitivity evaluation to the learning section 348 as a training signal, inputs the music to the learning section 348 as an input signal, and causes the learning section 348 to perform machine learning on a relation between the music and the sensitivity evaluation. By referring to the relation obtained by the machine learning by the learning section 348, the server 30 can automatically acquire the information regarding the sensitivity evaluation for the performance in the trial on the basis of the music (vibration and the like) by the performance in the trial. It is noted that, in the present embodiment, weighting may be performed in such a manner that the sensitivity evaluation of the professionals is reflected in the relation obtained by the machine learning more strongly than that of the nonprofessionals, or weighting may be performed conversely in such a manner that the sensitivity evaluation of the nonprofessionals is reflected in the relation obtained by the machine learning more strongly than that of the professionals. Moreover, in the present embodiment, the server 30 may input parameters (a key touch force, a key touch timing, a key touch length, and the like) of the key touch on the piano by a robot or the like and a sensitivity evaluation by the robot or the like for the sound, the music, and the like by the key touch to the learning section 348, cause the learning section 348 to perform machine learning on a relation between the sound and the like by the key touch by the robot or the like and the sensitivity evaluation by the robot or the like, and acquire the relation. In the present embodiment, referring to the machine learning in this way makes it possible to acquire the information regarding the sensitivity evaluation without bothering the performer.

(Step S209)

The server 30 writes the feature variables 506, the evaluation values 506a, and the information regarding the sensitivity evaluation acquired in Steps S205 and S207 to the metafile described above. In the present embodiment, linking the feature variables 506, the evaluation values 506a, and the information regarding the sensitivity evaluation to the sensing data group makes it possible to appropriately and easily manage the sensing data group and select the training data.

(Step S211)

As depicted in FIG. 10, the server 30 repeats Steps S201 to S209 described above, collects a plurality of sensing data groups (text files) 502 and metafiles 504 linked to the respective sensing data groups 502, and constructs the DB 372. As previously described, each sensing data group 502 in the DB 372 can be managed on the basis of the information contained in the metafile 504. As depicted in, for example, FIG. 11, each sensing data group 502 can be managed per performer (such as a pianist A or a pianist B) in a performance chronological order on the basis of the information contained in the metafile 504. It is noted that, in the present embodiment, a method of management is not limited to managing each sensing data group 502 per performer and that each sensing data group 502 can be managed under various conditions such as per title of music or per age.

(Step S213)

The server 30 creates the training data on the basis of the database 372 constructed in Step S211 described above. In the present embodiment, the training data can be created mainly from two methods.

In a first method, the sensing data 500 or the feature variables 506 obtained in one trial are used as the training data as it is or as they are.

In a second method, machine learning is performed using a plurality of pieces of sensing data 500 regarding a plurality of performers or a plurality of trials, thereby using a result obtained by the machine learning as the training data.

As depicted in, for example, FIG. 12, the server 30 inputs the sensing data groups 502 and the metafiles 504 each containing the evaluation values 506a to the learning section 348 as input signals and training signals, respectively. The learning section 348 performs machine learning on the relation between the plurality of pieces of sensing data 500 and the plurality of series of evaluation values 506a by performing multivariate analysis such as multiple regression analysis thereon. The learning section 348 may then output information regarding the relation (relation information) 608 obtained by performing the machine learning as the training data.

The plurality of pieces of sensing data 500 handled by the learning section 348 at this time are accurately synchronized with one another by the conversion apparatus 20 as previously described. Therefore, performing the multivariate analysis using the plurality of pieces of accurately synchronized sensing data 500 enables the learning section 348 to extract the sensing data 500 highly associated with the evaluation values 506a and to obtain the highly accurate relation information 608.

Furthermore, in the present embodiment, use of the relation information 608 indicating the relation between the sensing data 500 and the evaluation values 506a is not limited to use as the training data. For example, the server 30 inputs the feature variables 506 and the evaluation values 506a to the learning section 348 as input signals and training signals, respectively. As depicted in FIG. 13, the learning section 348 performs machine learning on the relation between the feature variables 506 and the evaluation values 506a by performing the multivariate analysis such as multiple regression analysis thereon. The learning section 348 may then output the information regarding the relation (relation information) 608 obtained by the machine learning described above as the training data.

In this way, in the present embodiment, using collective intelligence of the sensing data regarding the plurality of performers or the plurality of trials as the training data makes it possible to extract items of the sensing data 500 or the feature variables 506 that indicate characteristic tendency in performers at the high performance level and performers at the low performance level. It is noted that the relation information 608 described above may be not only used as the training data at the time of performing comparison in a subsequent step but also referred to at the time of selecting one or a plurality of pieces of training data from among a plurality of pieces of training data for the comparison.

It is noted that, at the time of performing the machine learning, the sensing time widths in the trials do not always match one another; thus, it is preferable for the server 30 to match the time widths of the sensing data in the trials with one another on the basis of, for example, the timing of touching the keys.

(2.6.2 Details of Creation of Comparison Data)

Next, FIG. 14 depicts details of creation of the comparison data in Step S300 of FIG. 6 described above. FIG. 14 is a flowchart of creating the comparison data according to the present embodiment. As depicted in FIG. 14, the creation of the comparison data includes a plurality of steps from Step S301 to Step S309. It is noted that Steps S301 to S309 of FIG. 14 correspond to Steps S201, S203, S207, S209, and S213 of FIG. 7; thus, detailed description thereof is omitted herein.

(2.6.3 Details of Comparison)

Figure 15:
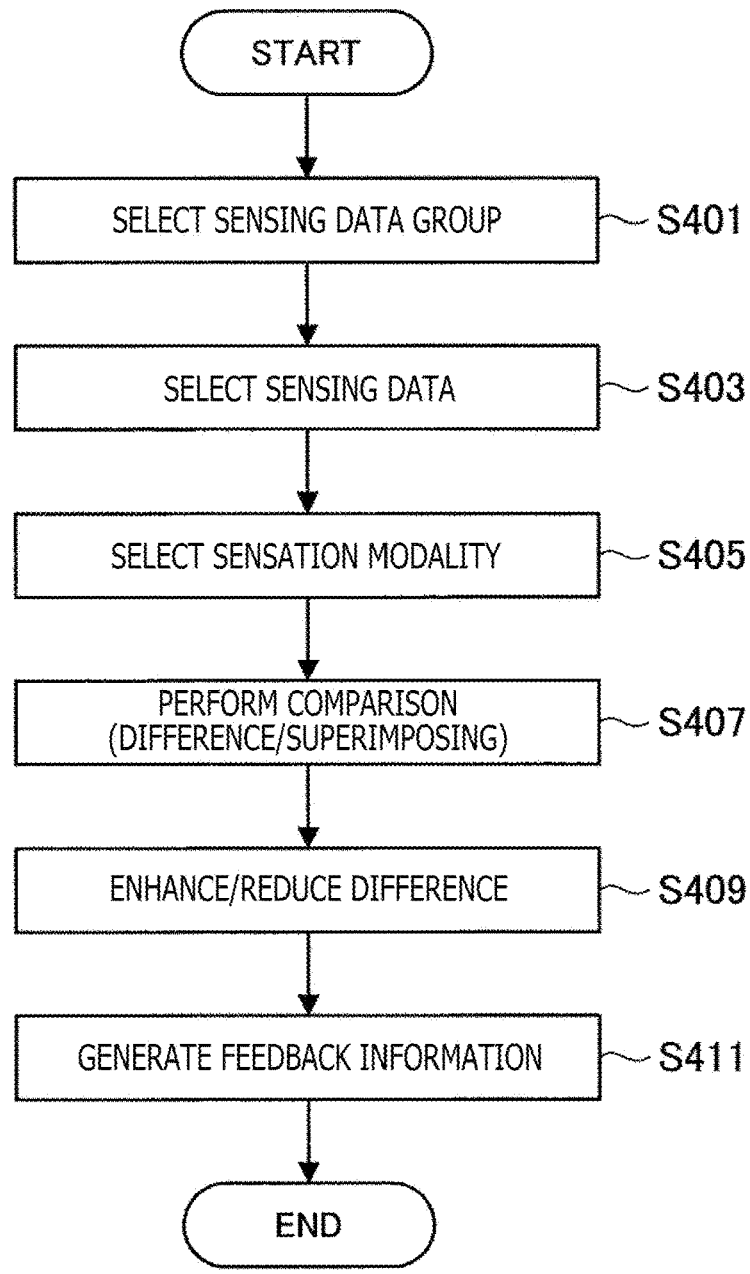
FIG. 15 is a flowchart of comparison according to the embodiment of the present disclosure.
Figure 16:
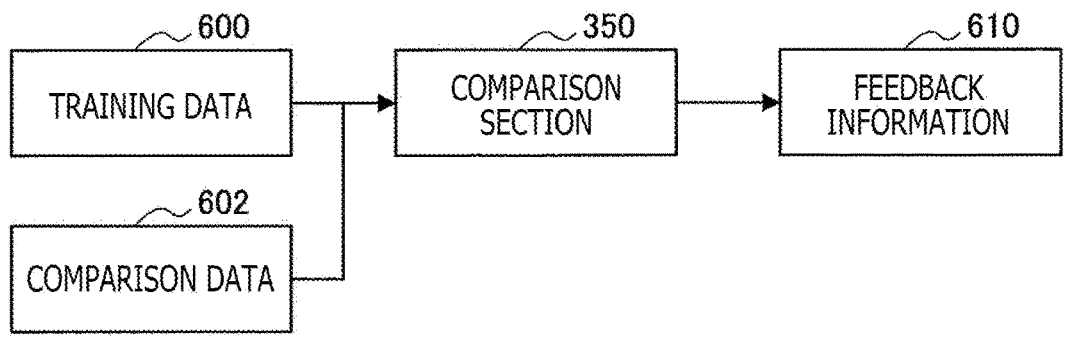
FIG. 16 is an explanatory diagram (1) of an example of comparison.
Figure 17:
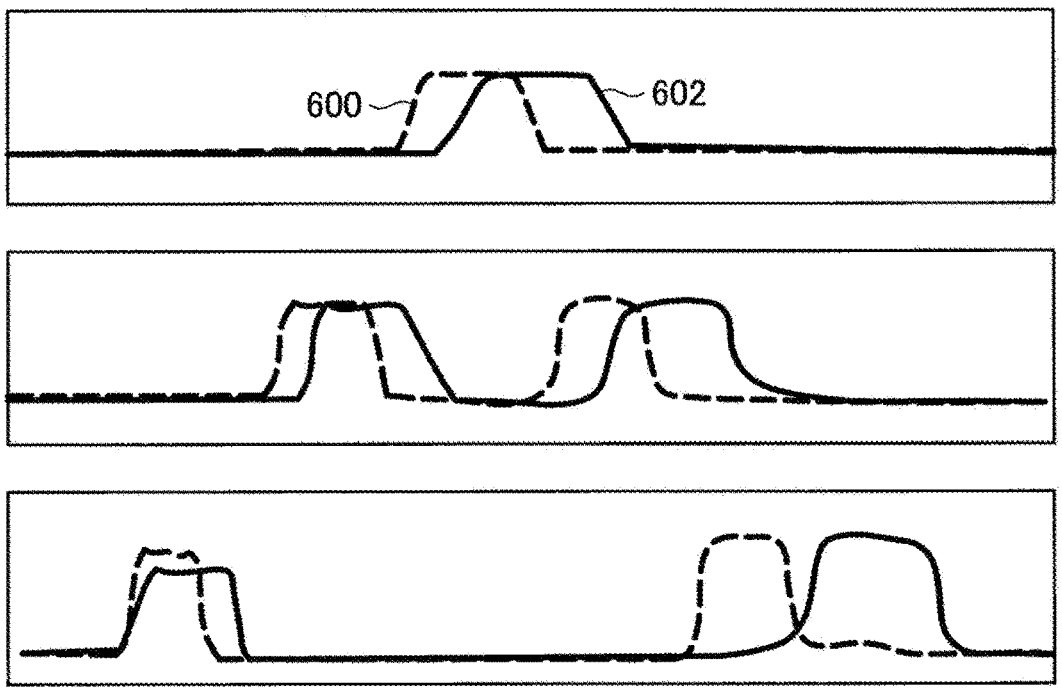
FIG. 17 is an explanatory diagram (2) of the example of comparison.

Details of the comparison in Step S400 of FIG. 6 described above will next be described with reference to FIGS. 15 to 17. FIG. 15 is a flowchart of the comparison according to the present embodiment and FIGS. 16 and 17 are explanatory diagrams of an example of the comparison. As depicted in FIG. 15, the comparison according to the present embodiment includes a plurality of steps from Step S401 to Step S411. Details of the steps will be described hereinafter.
(Step S401)
First, the server 30 selects the sensing data group 502 containing the test piece (the piece of music, the phrase, the scale, the arpeggio, the chord, or the like) performed by the learner or part of the test piece as selection of the training data from the DB 372. At this time, the server 30 can select the sensing data group 502 on the basis of the attribute information associated with the performance contained in the metafile 504. At this time, in the case of presence of a plurality of sensing data groups 502 in the DB 372, it is preferable that the server 30 creates a list of these plurality of sensing data groups 502 and displays the list to the user. The user then selects the sensing data group 502 desired to be used for comparison from the list. At this time, the user may select the sensing data group 502 related to a performance of a performer other than the learner or may select the sensing data group 502 related to a past performance of the learner.

Furthermore, in the case of presence of the plurality of sensing data groups 502 in the DB 372, the server 30 may extract the sensing data group 502 having attribute information regarding a performer similar to the attribute information (the gender, the age, the physical size, the muscle force, the tenderness, the legerity, and the like) regarding the learner according to the attribute information regarding the learner and the like, and recommend the extracted sensing data group 502 to the user. Alternatively, the server 30 may extract the sensing data group 502 having attribute information associated with the sensing and similar to the attribute information associated with the sensing (the sensor type, the sampling frequency, the number of channels, and the like) in the trial of the learner according to the attribute information in the trial of the learner and the like, and recommend the extracted sensing data group 502 to the user. In another alternative, the server 30 may extract the sensing data group 502 having attribute information regarding a trial similar to the attribute information regarding the trial (the competition name, the competition level, and the like) of the learner and attribute information regarding a user's desired trial (the attendance, the number of fans, the evaluation information regarding attendance, the number of views, and the like) according to these pieces of attribute information, and recommend the extracted sensing data group 502 to the user. In still another alternative, the server 30 may extract the sensing data group 502 according to the user's desired sensitivity evaluation and the evaluation values 506a for the performance, and recommend the extracted sensing data group 502 to the user. In the present embodiment, by doing so, it is possible to reduce the number of options for the user and for the user to easily select the sensing data group 502.
(Step S403)
Next, the user makes a selection as to the feature variables 506 regarding what part and what motion (for example, how to use muscles, a motion of the body, and the like) in a body movement are used for the comparison to realize a desired state of the performance (for example, fast piano playing like a famous pianist). In other words, the user selects one or a plurality of pieces of the sensing data 500, the feature variables 506, or the relation information 608 for use as the training data from the sensing data group 502 selected in Step S401 described above. At this time, there is a probability of presence of vast amounts of data that can be candidates of the training data in the sensing data group 502; thus, the server 30 may extract suitable training data and recommend the suitable training data to the user, or automatically select the suitable training data.

For example, the server 30 calculates a difference between each sensing data 500 in the sensing data group 502 selected in Step S401 and the sensing data 500 regarding the learner of the same item as that of the former sensing data 500. The server 30 then recommends to the user the sensing data 500 greatest in difference as the training data. Alternatively, for example, the server 30 may automatically select the sensing data 500 estimated to be highly related to the user's desired state of the performance (evaluation values 506a) by referring to the relation information 608 as the training data. In the present embodiment, by doing so, it is possible to reduce the number of options for the user and for the user to easily select the training data.
(Step S405)
Next, the user selects the sensation modality (the visual sensation, the auditory sensation, the tactile sensation, or the like) suited to feed back the feedback information generated in Step S411 to be described later to the user. In the present embodiment, the feedback information can be fed back, for example, by the visual sensation via the display apparatus, by the auditory sensation via the audio output apparatus, or by the tactile sensation via the wearable apparatus (haptic mechanism) attached to the body of the learner. Furthermore, in the present embodiment, the user may select a plurality of sensation modalities.
(Step S407)
Next, the server 30 performs comparison either by calculating the difference between the training data selected in Step S403 and the sensing data 500 (comparison data) regarding the learner of the item same as that of the training data, or by superimposing the training data on the comparison data. As depicted in, for example, FIG. 16, the comparison section 350 of the server 30 compares training data 600 with comparison data 602. In subsequent Step S411, feedback information 610 is then generated on the basis of a comparison result. It is noted that, in Step S407, the server 30 may calculate the difference between the selected training data 600 and the comparison data 602 as previously described, or superimpose the training data 600 on the comparison data 602 as depicted in FIG. 17.
(Step S409)
Next, the server 30 may emphasize or reduce the difference between the training data and the comparison data obtained in Step S407 described above by expanding or contracting the difference either spatially or temporally. Specifically, in the present embodiment, the difference is reduced by a predetermined contraction ratio for the learner at the skill level greater in difference from that in the training data 600 to avoid the decrease of motivation of learning. On the assumption, for example, that the key touch force in the training data 600 is 1, in a case in which the key touch force of the learner (comparison data) is approximately 80 lower than that in the training data, the server 30 provides the difference in key touch force contracted (reduced) to 20% without providing the difference kept at 80%. On the other hand, in the present embodiment, the small difference is expanded by a predetermined magnification for the learner at the skill level smaller in difference from that in the training data 600 to guide the learner to a higher skill level in such a manner that the learner can easily recognize the difference. For example, in a case in which the key touch timing of the learner (comparison data) is 0.01 seconds faster than that in the training data 600, the server 30 provides the difference expanded (emphasized) to 0.1 seconds without providing the difference kept at 0.01 seconds in such a manner that the learner can easily recognize the difference. In other words, in the present embodiment, performing the processing on the difference described above makes it possible for the learner to easily recognize the difference from the training data 600 while avoiding the decrease of the motivation of the learner; thus, it is possible to realize assistance of efficient learning of the performance. It is noted that the magnification or the contraction ratio for the difference may be adjusted step by step according to the change in the skill level of the learner in the present embodiment. Furthermore, temporal expansion or contraction means slowing down or speeding up the time associated with providing of the feedback information.

(Step S411)

The server 30 generates the feedback information 610 to be fed back to the user according to the processing from Step S401 to S409 described above.

2.7. Summary

As described so far, according to the embodiment of the present disclosure described above, it is possible to provide the information processing system 1 capable of accurately synchronizing and handling the sensing data in a mixture of forms and available for assisting in learning of the performance.

3. Learning Assistance Mode

Figure 18:
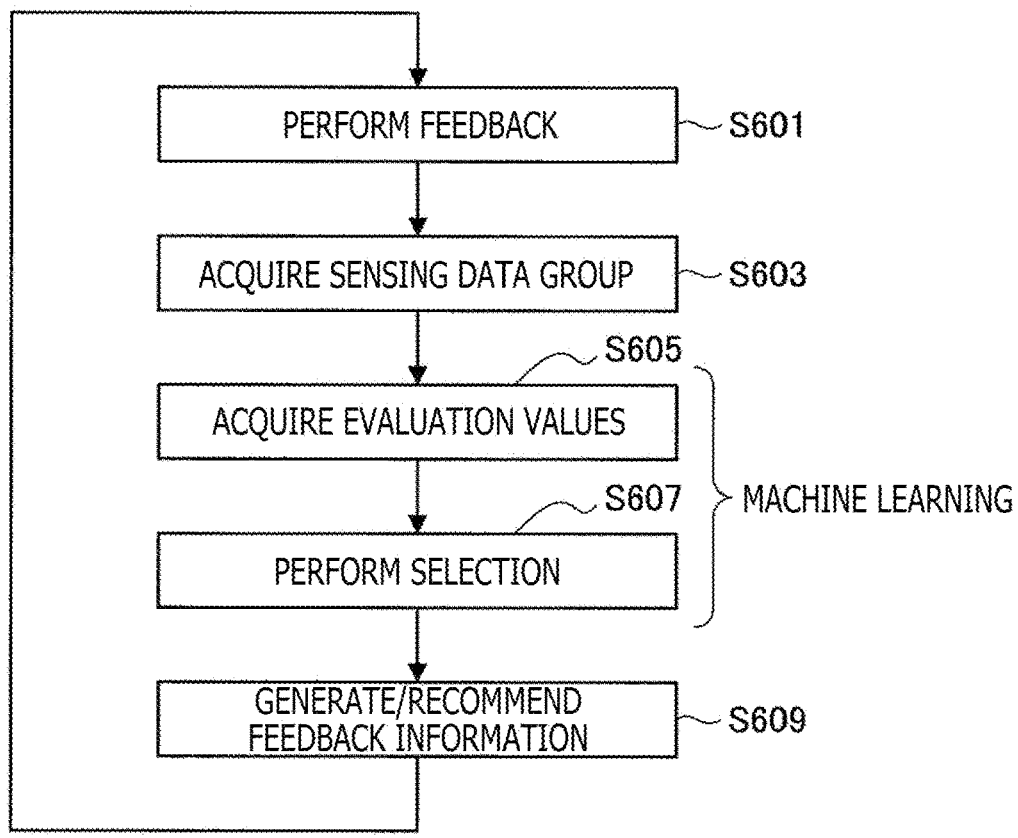
FIG. 18 is a flowchart of a learning assistance mode according to the embodiment of the present disclosure.

Meanwhile, in the embodiment of the present disclosure described above, it is preferable to provide a learning assistance mode to be described hereinafter such that effectiveness of the learning assistance based on the feedback provided by the information processing system 1 described above can be further enhanced. Therefore, the learning assistance mode according to the embodiment of the present disclosure will be described hereinafter with reference to FIG. 18. FIG. 18 is a flowchart of the learning assistance mode according to the present embodiment. It is assumed that the user can select in advance whether to execute the learning assistance mode.

Meanwhile, as elements associated with contents of the feedback information 610 among elements of the feedback that have an influence on the learning of the learner, items of the training data 600 used in the comparison (what sensing data 500 and what feature variables 506 are to be selected), a method of the comparison (whether the difference between the training data 600 and the comparison data 602 is calculated or these pieces of data are superimposed), and the like can be cited. Furthermore, as elements associated with output of the feedback information 610, a degree of emphasis or reduction of the difference, the sensation modality by which the feedback information is fed back, and the like can be cited. Which of these elements is more effective for the learning assistance in what way varies depending on the performance to be learned and characteristics and circumstances of the learner. In the acquisition assistance mode according to the present embodiment, therefore, which of the elements is more effective for the learning assistance in what way is searched in real time and higher effective feedback is provided.

For example, in a case in which the learner or the like is unable to realize a desired performance, a plurality of elements (feature variables) is often present as causes. In the case, for example, of a mistake in key touch during the performance, a plurality of elements that causes the mistake in the key touch is present including wrong forms of learner's arms, tensing up of the muscles, and delayed timing of looking at the keys to be touched. Therefore, an algorithm that can be obtained by the learning assistance mode makes it possible to select such an element that "the learner will be able to avoid making mistakes in the key touch at the earliest if correcting this element." For example, the algorithm selects the element for which the difference between the comparison data and the training data is the greatest among the plurality of factors (feature variables), or selects the feature variables said to be important according to experiences of many performers. Using such an algorithm enables the learning assistance to be performed more effectively.

For example, in the learning assistance mode, the learner is made to repeat trials of the same test piece approximately a few times (for example, three to five times), and the server 30 repeats acquisition and analysis of the sensing data group 502 and presentation of the feedback information 610.

At this time, the server 30 extracts the evaluation values 506*a* (state of the performance) for the performance of the learner from the sensing data 500, and calculates changes in evaluation values 506*a* from those in the previous trial. At this time, in a case in which it is not confirmed that the evaluation values 506*a* have improved, the server 30 changes the items of the training data 600 used in the comparison, the method of the comparison, the degree of the emphasis or the reduction of the difference, the sensation modality, and the like, and feeds back the changes before a next trial. On the other hand, in a case in which it is confirmed that the evaluation values 506*a* have improved, the server 30 feeds back the feedback information before the next trial without changing the training data 600 used in the comparison, the method of the comparison, the degree of the emphasis or the reduction of the difference, the sensation modality, and the like.

Furthermore, repeatedly carrying out such trials and feedback enables the learning section 348 of the server 30 to perform the machine learning on a relation of the evaluation values 506*a* with the items of the training data 600, the method of the comparison, the degree of the emphasis or the reduction of the difference, and the sensation modality. In other words, the learning section 348 can make it clear, by the machine learning, the items of the training data 600 used in the comparison, the method of the comparison, the degree of the emphasis or the reduction of the difference, the sensation modality, and the like suited for improving a state of a specific performance of the learner. Furthermore, the server 30 can select the suited items of the training data 600, the suited method of the comparison, the suited degree of the emphasis or the reduction of the difference, and the suited sensation modality using the algorithm based on the relation obtained by such machine learning, and recommend a selection result to the user. Moreover, the server 30 may apply the algorithm obtained in this way to another learner. For example, it is estimated that a learner, if similar in attribute information (the name, the gender, the age, the body height, the body weight, the physical size, the muscle force, the palm size, and the like), tends to have similar items of the training data 600 used in the comparison, a similar method of the comparison, a similar degree of the emphasis or the reduction of the difference, and a similar sensation modality suited for improving the state of the specific performance; thus, the server 30 may determine whether to apply the algorithm to the other learner on the basis of the attribute information regarding the other learner.

Furthermore, in the learning assistance mode, in a case in which there appears to be a correlation between an improvement of a motility function (the muscle force, joint ranges of motion, quickness, and sensory functions) of the learner and the improvement of the state of the specific performance, the server 30 preferably not only performs the feedback but also recommends a training for improving the motility function. For example, it is known that a performer ununiform in rhythm and incorrect in rhythm during the performance is lower in a tactile function of fingertips and lower in a function to independently move fingers. The server 30, therefore, recommends to the learner, as the training for improving the motility function, a finger independent moving exercise and a tactile function training (sensory learning training) in a case in which the learner aims to improve a performance, that is, "to improve strictness."

More specifically, as depicted in FIG. 18, the learning assistance mode according to the present embodiment includes a plurality of steps from Step S601 to Step S609. Details of these steps will be described hereinafter.

(Step S601)

The feedback apparatus 70 performs feedback toward the learner on the basis of the feedback information 610 received from the server 30, similarly to the above description.

(Step S603)

The learner executes a trial of the same test piece as that in a previous trial while referring to the feedback. The server 30 acquires the sensing data group 502 related to the executed trial.

(Step S605)

The server 30 extracts the evaluation values 506a for the performance of the learner on the basis of the sensing data group 502 acquired in Step S603 described above. Furthermore, the server 30 calculates changes in the evaluation values 506a from those in the previous trial.

(Step S607)

In the case in which it is not confirmed that the evaluation values 506a have improved, the server 30 selects to change the items of the training data 600 used in the comparison, the method of the comparison, the degree of the emphasis or the reduction of the difference, the sensation modality, and the like. On the other hand, in the case in which it is confirmed that the evaluation values 506a have improved, the server 30 selects not to change the items of the training data 600 used in the comparison, the method of the comparison, the degree of the emphasis or the reduction of the difference, the sensation modality, and the like.

At the time of Steps S605 and S607 described above, the server 30 performs the machine learning on the relation of the evaluation values 506a with the items of the training data 600, the method of the comparison, the degree of the emphasis or the reduction of the difference, and the sensation modality. As previously described, the server 30 may perform next feedback using the algorithm based on the relation obtained by the machine learning.

(Step S609)

Next, the server 30 generates the feedback information 610 on the basis of selection in Step S607 described above. Furthermore, the server 30 selects a training for improving the motility function to be recommended to the learner.

4. Examples of Application of Embodiment of Present Disclosure

The embodiment of the present disclosure has been described so far. Examples of application of the embodiment of the present disclosure will next be described more specifically. It is noted that the following examples of application are given as an example of the embodiment of the present disclosure only, and the embodiment of the present disclosure is not limited to the following examples of application.

As one example of application of the embodiment of the present disclosure, skill acquisition assistance of sports, arts (paintings, calligraphy, and the like), performing arts and traditional arts, various operation simulators (for motor vehicles, airplanes, and the like), and games can be cited besides the learning of musical instrument playing techniques. For example, attaching the sensor apparatus 10 described above to a tennis racket or the like enables identification of a skill element necessary to improve in a tennis performance of the user and automatic coaching to the user and the like.

Furthermore, as examples of application of the embodiment of the present disclosure, assistance of diagnosis of a patient affected with an impaired motility function, evaluation of effectiveness of treatment, and prediction assistance of a future impaired motility function can be cited. While it is known, for example, on a job site of music therapy that practice of musical instrument playing contributes to a recovery from a motility function or a cognitive function after a cerebral stroke, most of a mechanism of the recovery is not reached yet. In the present embodiment, therefore, it is also possible to accurately synchronize data associated with a brain activity of a patient with data associated with a movement such as the musical instrument playing, and acquire these pieces of data; thus, it is expected to acquire information beneficial for making the mechanism clear.

Moreover, the DB 372 constructed in the present embodiment is also beneficial for development of various types of coaching methods for skill learning; thus, the DB 372 could be a product to be traded solely.

5. Hardware Configurations

FIG. 19 is an explanatory diagram illustrating an example of a hardware configuration of an information processing apparatus 900 according to the present embodiment. In FIG. 19, the information processing apparatus 900 indicates an example of the hardware configuration of the server 30 described above.

The information processing apparatus 900 has, for example, a CPU 950, a ROM 952, a RAM 954, a recording medium 956, and an input/output interface 958. The information processing apparatus 900 further has a haptic device 960, a display device 962, an audio output device 964, a communication interface 968, and a sensor 980. Moreover, the information processing apparatus 900 connects the constituent elements to one another by, for example, a bus 970 that serves as a data transmission passage.

(CPU 950)

The CPU 950 is configured with, for example, one or two or more processors each including a computing circuit such as a CPU, every type of processing circuit, and the like, and functions as the main control section 340 that exercises control over the entire information processing apparatus 900.

(ROM 952 and RAM 954)

The ROM 952 stores therein programs, control data such as computing parameters, and the like used by the CPU 950. The RAM 954 temporarily stores therein the programs and the like executed by the CPU 950. The ROM 952 and the RAM 954 function as, for example, the storage section 370 described above in the information processing apparatus 900.

(Recording Medium 956)

The recording medium 956 functions as the storage section 370 described above, and stores, for example, data related to the information processing method according to the present embodiment, and various types of data such as various applications. Examples of the recording medium 956 include herein a magnetic recording medium such as a hard disk and a nonvolatile memory such as a flash memory. Furthermore, the recording medium 956 may be detachable from the information processing apparatus 900.

(Input/Output Interface 958, Haptic Device 960, Display Device 962, and Audio Output Device 964)

The input/output interface 958 connects, for example, the haptic device 960, the display device 962, the audio output device 964, and the like. Examples of the input/output interface 958 include a USB (Universal Serial Bus) terminal, a DVI (Digital Visual Interface) terminal, an HDMI (High-Definition Multimedia Interface) (registered trademark) terminal, and various types of processing circuits.

The haptic device 960 functions as the haptic mechanism 710 described above, the display device 962 functions as the display section 714 described above, and the audio output device 964 functions as the audio output section 716 described above. As the haptic device 960, a wearable device attached to the body of the learner can be cited. As the audio output device 964, a speaker, a headphone speaker, and the like can be cited. Furthermore, as the display device 962, a liquid crystal display, an organic EL display (Organic Electro-Luminescence Display), and the like can be cited.

Needless to say, the input/output interface 958 can be connected to an external device such as an operation input device (for example, a keyboard and a mouse) outside of the information processing apparatus 900 and an external display device.

(Communication Interface 968)

The communication interface 968 is communication means that functions as the communication section 360 and that is provided in the information processing apparatus 900, and functions as a communication section (not depicted) for holding either wireless or wired communication with an external apparatus via the network 90 (or directly). Examples of the communication interface 968 include a communication antenna, an RF (Radio Frequency) circuit (for wireless communication), an IEEE802.15.1 port and a transmitting-receiving circuit (for wireless communication), an IEEE8020.11 port and a transmitting-receiving circuit (for wireless communication), and a LAN (Local Area Network) terminal and a transmitting-receiving circuit (for wired communication).

The example of the hardware configuration of the information processing apparatus 900 has been illustrated so far. It is noted that the hardware configuration of the information processing apparatus 900 is not limited to the configuration depicted in FIG. 19. More specifically, the above constituent elements may be configured using general-purpose members, or configured by hardware dedicated to functions of the constituent elements. Such a configuration could be changed as appropriate according to technology levels at different times of carrying out the present disclosure.

For example, the information processing apparatus 900 is not necessarily configured with the communication interface 968 in the case of communication with an external apparatus or the like via an external communication device connected to the information processing apparatus 900 or in the case of being configured to perform processing in a stand-alone fashion. Furthermore, the communication interface 968 may be configured to be capable of communication with one or two or more external apparatuses by a plurality of communication schemes.

Moreover, the information processing apparatus according to the present embodiment may be applied to a system configured from a plurality of apparatuses on the premise of connection to a network such as cloud computing (or of communication between the apparatuses).

In other words, the information processing apparatus according to the present embodiment described above can be realized as, for example, an information processing system performing processing related to the information processing method according to the present embodiment using the plurality of apparatuses.

6. Supplemental Remarks

It is noted that the embodiment of the present disclosure described previously could include, for example, a program for causing a computer to function as the information processing apparatus (for example, the server 30) according to the present embodiment, and a non-transitory tangible medium recording therein a program. Furthermore, the program may be distributed via a communication line (including a line for wireless communication) such as the Internet.

Furthermore, the steps in each processing in the embodiment of the present disclosure described above are not necessarily processed in a described order. For example, the steps may be processed by changing the order as appropriate. Moreover, the steps may be partially processed either in parallel or individually as an alternative to be processed in time series. Furthermore, as for a method of processing the steps, the steps are not necessarily processed in accordance with the described method. For example, the steps may be processed by other methods by other functional sections.

While the preferred embodiment of the present disclosure has been described in detail with reference to the accompanying drawings, a technical scope of the present disclosure is not limited to such an example. It is obvious that a person skilled in the art is capable of contriving various types of modifications or correction examples within the scope of a technical concept described in claims, and it shall be comprehended that these respects naturally, also belong to the technical scope of the present disclosure.

It is noted that the following configurations fall in a technical range of the present disclosure.

(1) An information processing apparatus including:
  a conversion section that converts a plurality of pieces of sensing data in different forms obtained from a plurality of sensors each sensing a state related to a performance by a motion of a user;
  an information processing section that processes the sensing data converted by the conversion section; and
  an information output section that outputs feedback information to the user on the basis of a processing result of the information processing section, in which
  the conversion section includes
    an analog-digital signal conversion section that converts the sensing data in an analog form from the sensors into sensing data in a digital form and outputs the sensing data in the digital form to the information processing section, and
    a digital-analog signal conversion section that converts the sensing data in the digital form from the sensors into sensing data in the analog form and outputs the sensing data in the analog form to the analog-digital signal conversion section.

(2) The information processing apparatus according to (1), in which
the analog-digital signal conversion section has a first clock mechanism for synchronizing pieces of sensing data in the analog form from a first sensor that outputs the pieces of sensing data.

(3) The information processing apparatus according to (2), further including:
a second clock mechanism that is provided closer to a second sensor that outputs pieces of sensing data in the digital form for synchronizing the pieces of sensing data from the second sensor.

(4) The information processing apparatus according to (3), in which
the information processing section synchronizes the pieces of sensing data from the first sensor with the pieces of sensing data from the second sensor
on the basis of a temporal difference between the first clock mechanism and the second clock mechanism.

(5) The information processing apparatus according to (3) or (4), in which
the digital-analog signal conversion section converts the sensing data from the second sensor into sensing data in the analog form, and outputs the sensing data in the analog form to the first sensor as a trigger signal for driving the first sensor.

(6) The information processing apparatus according to any one of (3) to (5), in which
the first sensor includes at least one of
an acceleration sensor, a gyrosensor, an angular velocity sensor, a vibration sensor, a pressure sensor, a biological information sensor, a bending sensor, or a position sensor attached to a body of the user,
a pressure sensor or a photoreflector sensor that is mounted on an object moving by a motion of the user and that senses a movement of the object,
an imaging apparatus that images the user, or
a sound pick-up apparatus that senses a sound generated by the performance.

(7) The information processing apparatus according to (6), in which
the biological information sensor senses at least one of a heartbeat, a pulse, a brain wave, a respiration, a perspiration, a myoelectric potential, a skin temperature, a skin electrical resistance, an eyeball movement, a pupil diameter, or a nuclear magnetic resonance of the user.

(8) The information processing apparatus according to (6), in which
the object includes an acoustic musical instrument or an electronic musical instrument.

(9) The information processing apparatus according to any one of (3) to (8), in which
the second sensor includes at least one of
an acceleration sensor, a gyrosensor, an angular velocity sensor, a vibration sensor, a pressure sensor, a bending sensor, or a position sensor attached to a body of the user, or
an electronic musical instrument used by the user.

(10) The information processing apparatus according to any one of (1) to (9), further including:
a storage section that stores pieces of the sensing data output from the digital-analog signal conversion section while linking the pieces of the sensing data to pieces of attribute information regarding the pieces of the sensing data.

(11) The information processing apparatus according to (10), in which
the attribute information contains at least one of attribute information associated with the user, attribute information associated with the performance, feature variables characterizing the performance, evaluation information for the performance, attribute information associated with the sensing, or sensitivity evaluation information for the performance.

(12) The information processing apparatus according to (11), in which
the information processing section has an analysis section that analyzes the sensing data output from the digital-analog signal conversion section and extracts feature variables characterizing a state of the performance.

(13) The information processing apparatus according to (11), in which
the sensitivity evaluation information for the performance is input by the user every time the performance is given.

(14) The information processing apparatus according to (11), in which
the sensitivity evaluation information for the performance is acquired on the basis of the state related to the performance by referring to a relation between the state related to the performance and a sensitivity evaluation obtained by machine learning in advance.

(15) The information processing apparatus according to (11), in which
the evaluation information for the performance includes proportions of numerical values related to different types of the evaluation information for the performance, the different types of the evaluation information being in a trade-off relation.

(16) The information processing apparatus according to any one of (10) to (15), in which
the information processing section has a comparison section that selects, as training data, one or a plurality of pieces of the sensing data from among the plurality of pieces of the sensing data stored in the storage section and compares the selected training data with comparison data that is the sensing data which is related to the performance of the user and which is newly sensed.

(17) The information processing apparatus according to (16), in which
the comparison section compares the training data with the comparison data by calculating a difference between the training data and the comparison data or by superimposing the training data on the comparison data.

(18) The information processing apparatus according to (17), in which
the information output section outputs, as the feedback information, the difference on which emphasis or reducing processing has been performed.

(19) The information processing apparatus according to (18), in which
the information output section outputs the feedback information via at least one of a display apparatus, a wearable apparatus attached to a body of the user, or an audio output apparatus.

(20) The information processing apparatus according to (19), in which
the information processing section changes at least one of the sensing data used as the training data, a method of comparison by the comparison section, the processing performed on the difference, or the apparatus that outputs the feedback information on the basis of a change in a state of the performance of the user.

REFERENCE SIGNS LIST

1: Information processing system
10: Sensor apparatus
20: Conversion apparatus
26: Computing apparatus
30: Server
70: Feedback apparatus
90: Network
100: Sensor section
140, 340, 740: Main control section
142, 342: Data acquisition section
144, 344: Processing section
152, 352: Output control section
160, 360, 760: Communication section
200: D/A signal conversion section
202: D/A converter
210: A/D signal conversion section
212: A/D converter
214, 272: Clock
260: Receiving section
270: Computing section
300: Input section
310: Output section
346: Analysis section
348: Learning section
350: Comparison section
370, 770: Storage section
372: DB
500: Sensing data
502: Sensing data group
504: Metafile
506: Feature variable
506a: Evaluation value
600: Training data
602: Comparison data
608: Relation information
610: Feedback information
710: Haptic mechanism
714: Display section
716: Audio output section
900: Information processing apparatus
950: CPU
952: ROM
954: RAM
956: Recording medium
958: Input/output interface
960: Haptic device
962: Display apparatus
964: Audio output device
968: Communication interface
970: Bus
980: Sensor

The invention claimed is:

1. An information processing apparatus comprising:
a conversion section configured to convert a plurality of pieces of sensing data in different forms obtained from a plurality of sensors each sensing a state related to a performance by a motion of a user;
an information processing section configured to process the sensing data converted by the conversion section; and
an information output section configured to output feedback information to the user on a basis of a processing result of the information processing section, wherein
the conversion section includes
an analog-digital signal conversion section configured to convert the sensing data in an analog form from analog sensors of the plurality of sensors configured to output the sensing data in the analog form into converted sensing data in a digital form and output the converted sensing data in the digital form to the information processing section, and
a digital-analog signal conversion section configured to convert the sensing data in the digital form from digital sensors of the plurality of sensors configured to output the sensing data in the digital form into converted sensing data in the analog form and output the converted sensing data in the analog form to the analog-digital signal conversion section,
the analog-digital signal conversion section is further configured to convert the converted sensing data in the analog form converted from the sensing data in the digital form outputted from the digital sensors into the converted sensing data in the digital form,
the digital-analog signal conversion section is further configured to output the converted sensing data in the analog form to the analog sensors as a trigger signal for driving the analog sensors, and
the conversion section, the information processing section, the information output section, the analog-digital signal conversion section, and the digital-analog signal conversion section are each implemented via at least one processor.

2. The information processing apparatus according to claim 1, wherein
the analog-digital signal conversion section includes a first clock mechanism configured to synchronize pieces of sensing data in the analog form from a first sensor that outputs the pieces of sensing data in the analog form.

3. The information processing apparatus according to claim 2, further comprising:
a second clock mechanism configured to synchronize pieces of sensing data from a second sensor that outputs the pieces of sensing data in the digital form.

4. The information processing apparatus according to claim 3, wherein
the information processing section is further configured to synchronize the pieces of sensing data from the first sensor with the pieces of sensing data from the second sensor on a basis of a temporal difference between the first clock mechanism and the second clock mechanism.

5. The information processing apparatus according to claim 3, wherein
the first sensor includes at least one of
an acceleration sensor, a gyrosensor, an angular velocity sensor, a vibration sensor, a pressure sensor, a biological information sensor, a bending sensor, or a position sensor attached to a body of the user,
a pressure sensor or a photoreflector sensor that is mounted on an object moving by a motion of the user and that senses a movement of the object,
an imaging apparatus that images the user, or
a sound pick-up apparatus that senses a sound generated by the performance.

6. The information processing apparatus according to claim 5, wherein
the biological information sensor senses at least one of a heartbeat, a pulse, a brain wave, a respiration, a perspiration, a myoelectric potential, a skin temperature, a skin electrical resistance, an eyeball movement, a pupil diameter, or a nuclear magnetic resonance of the user.

7. The information processing apparatus according to claim 5, wherein
the object includes an acoustic musical instrument or an electronic musical instrument.

8. The information processing apparatus according to claim 3, wherein
the second sensor includes at least one of
an acceleration sensor, a gyrosensor, an angular velocity sensor, a vibration sensor, a pressure sensor, a bending sensor, or a position sensor attached to a body of the user, or
an electronic musical instrument used by the user.

9. The information processing apparatus according to claim 1, further comprising:
a memory configured to store pieces of the sensing data output from the digital-analog signal conversion section while linking the pieces of the sensing data to pieces of attribute information regarding the pieces of the sensing data.

10. The information processing apparatus according to claim 9, wherein
the attribute information contains at least one of attribute information associated with the user, attribute information associated with the performance, feature variables characterizing the performance, evaluation information for the performance, attribute information associated with the sensing, or sensitivity evaluation information for the performance.

11. The information processing apparatus according to claim 10, wherein
the information processing section includes an analysis section configured to analyze the sensing data output from the digital-analog signal conversion section and extract feature variables characterizing a state of the performance, and
the analysis section is implemented via at least one processor.

12. The information processing apparatus according to claim 10, wherein
the sensitivity evaluation information for the performance is input by the user every time the performance is given.

13. The information processing apparatus according to claim 10, wherein
the sensitivity evaluation information for the performance is acquired on a basis of the state related to the performance by referring to a relation between the state related to the performance and a sensitivity evaluation obtained by machine learning in advance.

14. The information processing apparatus according to claim 10, wherein
the evaluation information for the performance includes proportions of numerical values related to different types of the evaluation information for the performance, the different types of the evaluation information being in a trade-off relation.

15. The information processing apparatus according to claim 9, wherein
the information processing section includes a comparison section configured to select, as training data, one or a plurality of pieces of the sensing data from among the plurality of pieces of the sensing data stored in the memory and compare the selected training data with comparison data that is the sensing data which is related to the performance of the user and which is newly sensed, and
the comparison section is implemented via at least one processor.

16. The information processing apparatus according to claim 15, wherein
the comparison section is further configured to compare the training data with the comparison data by calculating a difference between the training data and the comparison data or by superimposing the training data on the comparison data.

17. The information processing apparatus according to claim 16, wherein
the information output section is further configured to output, as the feedback information, the difference on which emphasis or reducing processing has been performed.

18. The information processing apparatus according to claim 17, wherein
the information output section is further configured to output the feedback information via at least one of a display apparatus, a wearable apparatus attached to a body of the user, or an audio output apparatus.

19. The information processing apparatus according to claim 18, wherein
the information processing section is further configured to change at least one of the sensing data used as the training data, a method of comparison by the comparison section, the processing performed on the difference, or the apparatus that outputs the feedback information on a basis of a change in a state of the performance of the user.

20. An information processing apparatus comprising:
a conversion section configured to convert a plurality of pieces of sensing data in different forms obtained from a plurality of sensors each sensing a state related to a performance by a motion of a user;
an information processing section configured to process the sensing data converted by the conversion section;
an information output section configured to output feedback information to the user on a basis of a processing result of the information processing section, wherein
the conversion section includes
an analog-digital signal conversion section configured to convert the sensing data in an analog form from the sensors into sensing data in a digital form and output the sensing data in the digital form to the information processing section, and
a digital-analog signal conversion section configured to convert the sensing data in the digital form from the sensors into sensing data in the analog form and output the sensing data in the analog form to the analog-digital signal conversion section,
the analog-digital signal conversion section includes a first clock mechanism configured to synchronize pieces of sensing data in the analog form from a first sensor that output the pieces of sensing data in the analog form; and
a second clock mechanism configured to synchronize pieces of sensing data in the digital form from a second sensor that outputs the pieces of sensing data in the digital form, wherein the information processing section is further configured to synchronize the pieces of sensing data from the first sensor with the pieces of sensing data from the second sensor on a basis of a temporal difference between the first clock mechanism and the second clock mechanism, the digital-analog signal conversion section is further configured to convert the sensing data from the second sensor into sensing data in the analog form, and output the sensing data in the analog form to the first sensor as a trigger signal for driving the first sensor, and the conversion section, the information processing section, the information output section, the analog-digital signal conversion section, and the digital-analog signal conversion section are each implemented via at least one processor.

* * * * *